United States Patent
Isab et al.

(10) Patent No.: US 9,796,734 B2
(45) Date of Patent: Oct. 24, 2017

(54) GOLD(III) ANTI-CANCER AGENTS

(71) Applicant: KING FAHD UNIVERSITY OF PETROLEUM AND MINERALS, Dhahran (SA)

(72) Inventors: Anvarhusein A. Isab, Dhahran (SA); Muhammad Altaf, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 0 days.

(21) Appl. No.: 15/492,698

(22) Filed: Apr. 20, 2017

(65) Prior Publication Data

US 2017/0217994 A1    Aug. 3, 2017

Related U.S. Application Data

(62) Division of application No. 15/367,416, filed on Dec. 2, 2016, now Pat. No. 9,657,035.

(60) Provisional application No. 62/262,550, filed on Dec. 3, 2015.

(51) Int. Cl.
| | |
|---|---|
| *A61K 31/28* | (2006.01) |
| *C07F 1/00* | (2006.01) |
| *C12Q 1/68* | (2006.01) |
| *G01N 33/574* | (2006.01) |

(52) U.S. Cl.
CPC .................. *C07F 1/005* (2013.01)

(58) Field of Classification Search
CPC ...................................................... C07F 1/005
See application file for complete search history.

(56) References Cited

U.S. PATENT DOCUMENTS 9,487,542 B1 * 11/2016 Al-Jaroudi ................ C07F 1/12
9,585,861 B1 *  3/2017 Al-Jaroudi ............. C07F 1/005

OTHER PUBLICATIONS

Al-Jaroudi et al. New Journal of Chemistry (2014), 38(7) p. 3199-3211 (Provided by Applicants).*
M. Arsenijevic, et al., "Cytotoxicity of gold(III) complexes on A549 human lung carcinoma epithelial cell line" Medicinal Chemistry, 2012, vol. 8, Issue.1, pp. 2-8.
S.S. Al-Jaroudi, et al., "Synthesis, spectroscopic characterization, X-ray structure and electrochemistry of new bis(1,2-diaminocyclohexane)gold(III) chloride compounds and their anti-cancer activities against PC3 and SGC7901 cancer cell lines" New J. Chem, 2014,38, pp. 3199-3211.

* cited by examiner

*Primary Examiner* — Yong Chu
(74) *Attorney, Agent, or Firm* — Oblon, McClelland, Maier & Neustadt, L.L.P.

(57) ABSTRACT

A method for treating cancer and gold(III) complexes with diaminocyclohexane ligand as anticancer agents. Also described are a pharmaceutical composition incorporating the gold(III) complexes and a method of synthesizing the gold(III) complexes.

6 Claims, 8 Drawing Sheets

Dashed lines represent hydrogen bonds

Dashed lines represent hydrogen bonds

Dashed lines represent hydrogen bonds

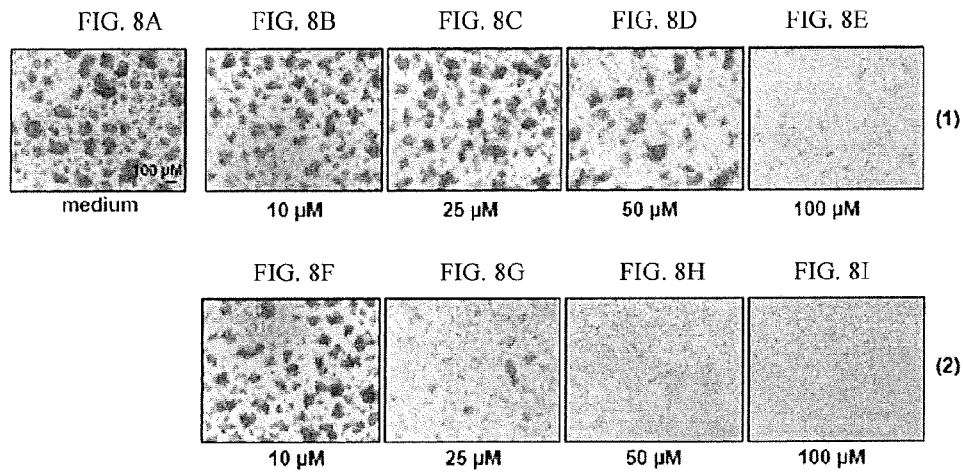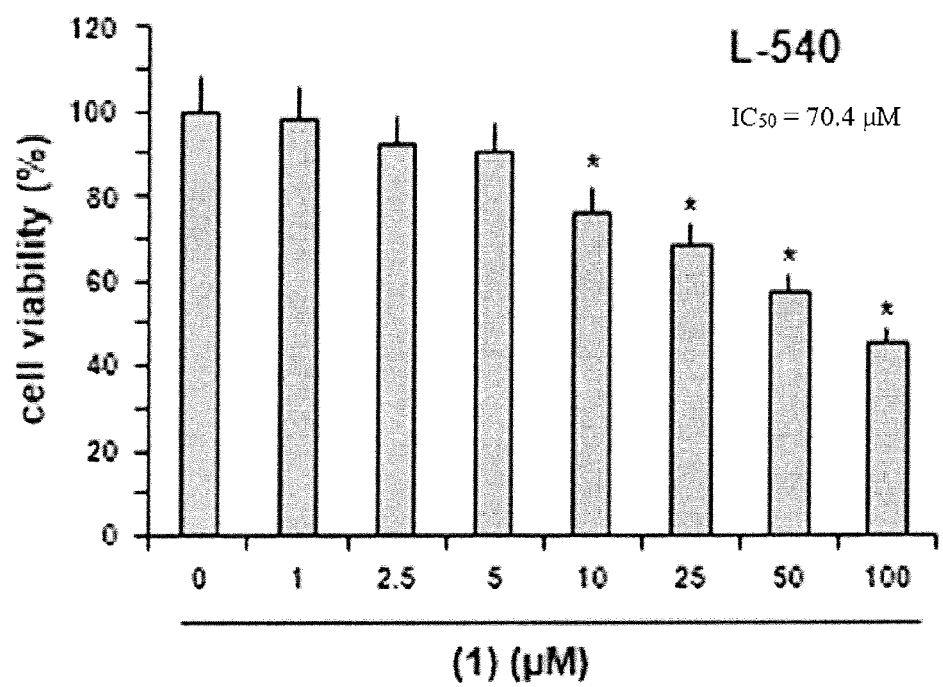

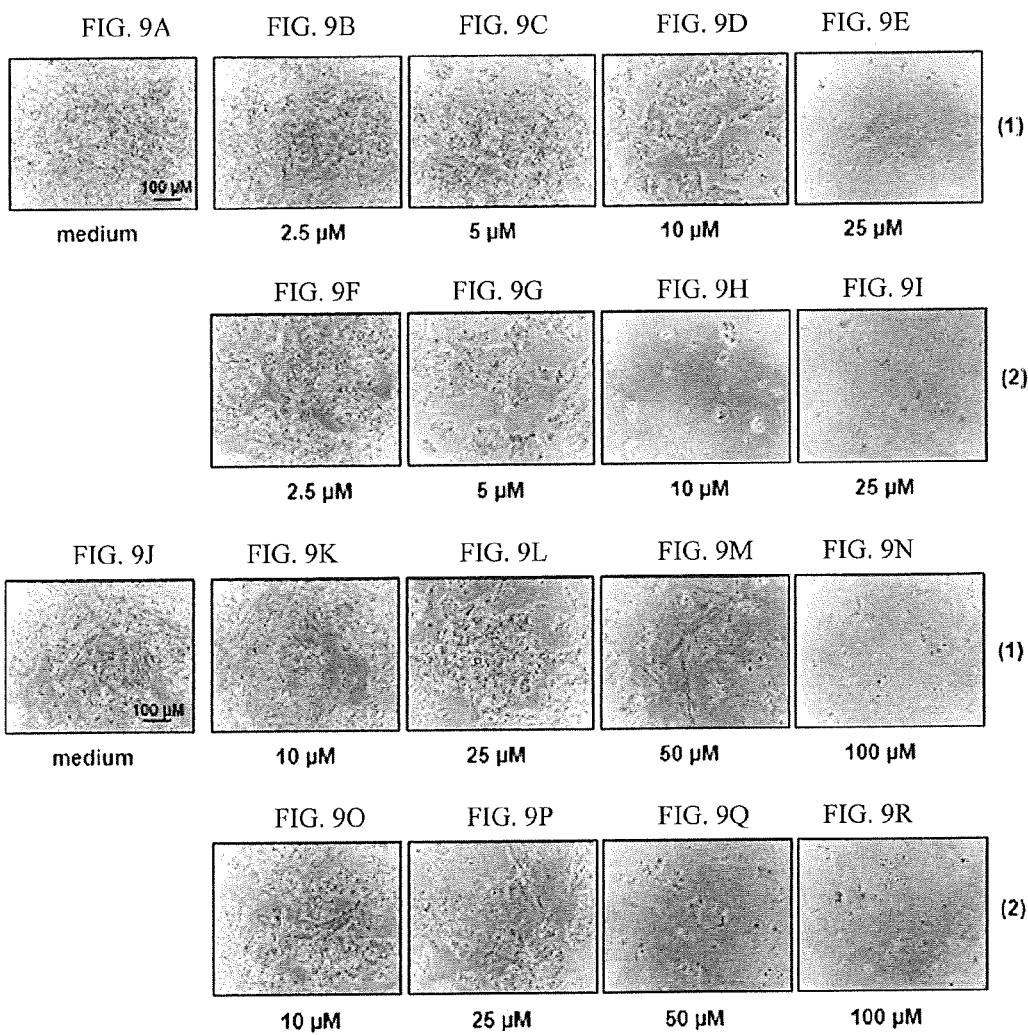

GOLD(III) ANTI-CANCER AGENTS

CROSS-REFERENCE TO RELATED APPLICATION

This application is a division of 15/367,416, now U.S. Pat. No. 9,657,035, having a filing date of Dec. 2, 2016and claiming priority to U.S. provisional application no. 62/262,550 having a filing date of Dec. 3, 2015, the disclosure of which is hereby incorporated by reference.

STATEMENT OF FUNDING ACKNOWLEDGEMENT

This project was funded by the National Plan for Science and Innovation (MARIFAH)-King Abdulaziz City for Science and Technology (KACST) through the Science and Technology Unit at King Fand University of Petroleum and Minerals (KFUPM) of Saudi Arabia, award No. 14-MED64-04.

BACKGROUND OF THE DISCLOSURE

Technical Field

The present disclosure relates to gold(III) complexes with anti-cancer activity and a method of treating cancer.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

One of the most important areas of study in contemporary bioinorganic chemistry is the development of new metal-based drugs (S. L. Best and P. J. Sadler, Gold Bull., vol. 29, no. 3, pp. 87-93, 1996; A. Casini, G. Kelter, C. Gabbiani, M. A. Cinellu, G. Minghetti, D. Fregona, H.-H. Fiebig, and L. Messori, J. Bio. Inorg. Chem., vol. 14, no. 7, pp. 1139-1149, 2009; S. H. van Rijt and P. J. Sadler, Drug Discov. Today, vol. 14, no. 23-24, pp. 1089-97, 2009; X. Wang and Z. Guo, Dalton Trans., no. 12, pp. 1521-32, 2008; C. Frank Shaw III, Chem. Rev., vol. 99, no. I, pp. 2589-2600, 1999; P. J. Sadler and R. E. Sue, Met. Based Drugs, vol. 1, pp. 107-44, 1994; I. Ott, Coord. Chem. Rev., vol. 253, no. 11-12, pp. 1670-1681, 2009; A. C. and L. M. Chiara Gabbiani, Gold Bull, vol. 40, pp. 73-81, 2007; M. A. Cinellu, L. Maiore, M. Manassero, A. Casini, M. Arca, H.-H. Fiebig, G. Kelter, E. Michelucci, G. Pieraccini, C. Gabbiani, and L. Messori, ACS Med Chem. Lett., vol. 1, no. 7, pp. 336-339, 2010; and A. Bindoli, M. P. Rigobello, G. Scutari, C. Gabbiani, A. Casini, and L. Messori, Coord. Chem. Rev., vol. 253, no. 11-12, pp. 1692-1707, 2009, each incorporated herein by reference in their entirety). Despite the successful use of cisplatin as a chemotherapy agent, side effects and resistance have been observed (A. Casini, C. Hartinger, C. Gabbiani, E. Mini, P. J. Dyson, B. K. Keppler, and L. Messori, J. Inorg. Biochem., vol. 102, no. 3, pp. 564-575, 2008; and V. Milacic, D. Fregona, and Q. P. Dou, Histol. Histopathol., vol. 23, no. 1, pp. 101-108, 2008, each incorporated herein by reference in their entirety). The use of gold in anti-rheumatic treatment supports its pharmaceutical importance (M. W. Whitehouse, Inflammopharmacology, vol. 16, no. 3, pp. 107-9, 2008; G. G. Graham, M. W. Whitehouse, and G. R. Bushell, Inflammopharmacology, vol. 16, no. 3, pp. 126-32, 2008; A. Casini, M. A. Cinellu, G. Minghetti, C. Gabbiani, M. Coronnello, E. Mini, and L. Messori, J. Med. Chem., vol. 49, no. 18, pp. 5524-31, 2006; and L. Ronconi, L. Giovagnini, C. Marzano, F. Bette, R. Graziani, G. Pilloni, and D. Fregona, Inorg. Chem., vol. 44, no. 6, pp. 1867-81, 2005, each incorporated herein by reference in their entirety). Recent studies have shown that several gold(III) complexes are highly cytotoxic against different tumor cells (L. Giovagnini, L. Ronconi, D. Aldinucci, D. Lorenzon, S. Sitran, and D. Fregona, J. Med. Chem., vol. 48, no. 5, pp. 1588-95, 2005; A. Casini, M. A. Cinellu, G. Minghetti, C. Gabbiani, M. Coronnello, E. Mini, and L. Messori, J. Med. Chem., vol. 49, no. 18, pp. 5524-5531, 2006; and D. Saggioro, M. P. Rigobello, L. Paloschi, A. Folda, S. A Moggach, S. Parsons, L. Ronconi, D. Fregona, and A. Bindoli, Chem. Biol., vol. 14, no. 10, pp. 1128-39, 2007, S. S. Al-Jaroudi, M. Monim-ul-Mehboob, M. Altaf, M. Fettouhi, M. I. M. Wazeer, S. Altuwaijri, and A. A. Isab, New J. Chem., vol 38, pp. 3199-3211, 2014; M. Arsenijevic, M. Milovanovic, V. Volarevic, A. Djekovic, T. Kanjevac, N. Arsenijevic, S. Dukic, Z. D. Bugarcic, Med. Chem., vol. 8, no. 1, pp. 2-8, 2012, each incorporated herein by reference in their entirety). Oxaliplatin, a platinum-based drug, is coordinated to (1R,2R)-(−)-1,2-diaminocyclohexane and a labile oxalate ligand (G. Sava, A. Bergamo, and P. J. Dyson, Dalton Trans., vol. 40, no. 36, pp. 9069-75, 2011; and L. Kelland, Nat. Rev. Cancer, vol. 7, no. 8, pp. 573-84, 2007, each incorporated herein by reference in their entirety).

Interactions of gold(III) complexes with biomolecules, such as sulfur-containing amino acids, thiols, or thioethers, are thought to be the cause of the cytotoxic effect of gold(III) complexes (A. V. Vujačić, J. Z. Savić, S. P. Sovilj, K. Mészáros Szécsényi, N. Todorović, M. Ž. Petković, and V. M. Vasić, Polyhedron, vol. 28, no. 3, pp. 593-599, 2009, incorporated herein by reference in its entirety). The toxic effects arise due to the coordination of the thiol and thioether groups of the side chains in proteins, peptides and amino acids followed by the reduction of gold(III) to gold(I) and subsequently to toxic gold(0) (T. Kolev, B. B. Koleva, S. Y. Zareva, and M. Spiteller, Inorg. Chien. Acta, vol. 359, no. 13, pp. 4367-4376, 2006; J. Zou, Z. Guo, J. A. Parkinson, Y. Chen, and P. J. Sadler, Chem. Commun., vol. 8, pp. 1359-1360, 1999; J. A. Cuadrado, W. Zhang, W. Hang, and V. Majidi, J. Env. Monit, vol. 2, no. 4, pp. 355-359, 2000; and P. L. Witkiewicz. and C. F. Shaw. III, J. Chem. Soc. Chem. commun, pp. 1111-1114, 1981, each incorporated herein by reference in their entirety). The electrochemistry of the interaction of guanosine-5-phosphate with gold(III) ethylenediamine complexes was studied by Zhu et al. (S. Zhu, W. Gorski, D. R. Powell, and J. A. Walmsley, Inorg. Chem., vol. 45, no. 6, pp. 2688-2694, 2006, incorporated herein by reference in its entirety). The interaction of the dipeptide Gly-Met with gold(III) ethylenediamine showed the formation of Gly-Met sulfoxide along with a free ethylenediamine ligand through a two-step decomposition reaction (B. Đ. Glišić, M. I. Djuran, Z. D. Stanić, and S. Rajković, Gold Bull, vol. 47, no. 1-2, pp. 33-40, 2014, incorporated herein by reference in its entirety). The substitution and reduction steps for the reaction of some gold(III) complexes with the biological thiols, L-cysteine, L-methionine, and glutathione were studied in detail by Durović et al. (M. D. Durović, Z. D. Bugarčić, F. W. Heinemann, and R. van Eldik, Dalton. trans., vol. 43, no. 10, pp. 3911-21, 2014, incorporated herein by reference in its entirety). The interaction between $[Au(CN)_4]^-$ and glutathione (GSH) at pH 7.4 showed the reduction of gold(III) to gold(I) along with the dimerization of GSH into its disulfide ($GSSG^{2-}$) derivative as the reaction product through a two-step decomposition reaction (P. M.

Yangyuoru, J. W. Webb, and C. F. Shaw, *J. Inorg. Biochem.*, vol. 102, no. 3, pp. 584-93, 2008; and B. A. Al-Maythalony, M. I. M. Wazeer, and A. A. Isab, *Inorg. Chim. Acta*, vol. 363, no. 13, pp. 3244-3253, 2010, each incorporated herein by reference in their entirety).

Therefore, it is an objective of this disclosure to provide gold(III) complexes with anti-cancer activity and a method for treating cancer.

BRIEF SUMMARY

The foregoing paragraphs have been provided by way of general introduction, and are not intended to limit the scope of the following claims. The described embodiments, together with further advantages, will be best understood by reference to the following detailed description taken in conjunction with the accompanying drawings.

The first aspect of the disclosure relates to a method for treating cancer, comprising administering an effective amount of at least one of a gold(III) complex represented by formula (I), a gold(III) complex represented by formula (II):

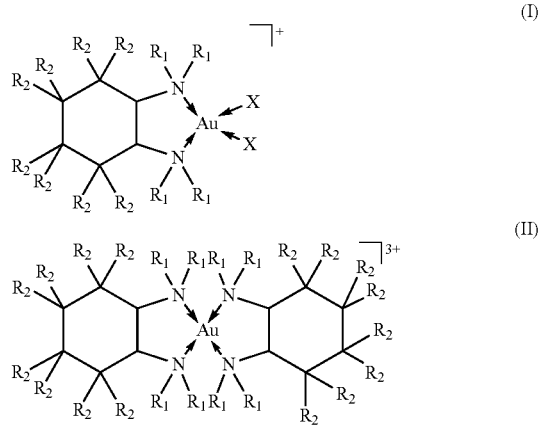

a pharmaceutically acceptable salt, solvate, prodrug, or a combination thereof to a subject;

where the cancer is ovarian cancer, Hodgkin lymphoma, or both;

each of $R_1$ is independently a hydrogen, an optionally substituted $C_1$-$C_8$ alkyl group, or an optionally substituted $C_6$-$C_8$ aryl group;

each of $R_2$ is independently a hydrogen, a halogen, a hydroxyl, an amino, a nitro, a cyano, an optionally substituted alkyl, an optionally substituted cycloalkyl, an optionally substituted heterocyclyl, an optionally substituted arylalkyl, an optionally substituted heteroaryl, an optionally substituted alkoxyl, an optionally substituted aryl, an optionally substituted alkenyl, a N-monosubstituted amino group, or a N,N-disubstituted amino group; and X is at least one pharmaceutically acceptable anion, such as chloride, bromide, and iodide.

In one embodiment, $R_1$ is hydrogen.

In one embodiment, $R_2$ is hydrogen.

In one embodiment, X is chloride.

In one embodiment, the gold(III) complex represented by formula (I) is

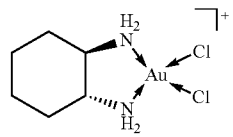

and the gold(III) complex represented by formula (II) is

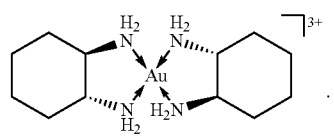

In one embodiment, the gold(III) complex represented by formula (I) or the gold(III) complex represented by formula (II) is administered as a salt having at least one counterion which is at least one pharmaceutically acceptable anion selected from the group consisting of fluoride, chloride, bromide, iodide, nitrate, sulfate, phosphate, methanesulfonate, ethanesulfonate, p-toluenesulfonate, salicylate, malate, maleate, succinate, tartrate, citrate, acetate, perchlorate, trifluoromethanesulfonate, acetylacetonate, hexafluorophosphate, and hexafluoroacetylacetonate.

In one embodiment, the at least one counterion is chloride.

In one embodiment, the ovarian cancer is resistant to cisplatin.

In one embodiment, the Hodgkin lymphoma is classical Hodgkin lymphoma.

In one embodiment, the method further comprises measuring a concentration of a biomarker and/or detecting a mutation in the biomarker before and/or after the administering.

In one embodiment, the biomarker is at least one selected from the group consisting of BRCA1, BRCA2, CCL17, CD163, CD30, NF-κB, Gal-1 CA125 HE4, mesothelin, transthyretin, ApoA1, VCAM, IL-6, IL-8, B7-H4, serum amyloid A, transferrin, osteopontin, kallikreins, OVX1, VEGF, AGR-2, inhibin, M-CSF, uPAR, EGF receptor, lysophosphatidyl acid, beta2-microglobulin, miRNA, and Epstein-Barr virus DNA.

In one embodiment, the concentration of the biomarker is measured with an ELISA assay and/or the mutation in the biomarker is measured with a PCR assay.

In one embodiment, the subject is a mammal.

In one embodiment, the effective amount of the at least one of the gold(III) complex represented by formula (I), the gold(III) complex represented by formula (II), the pharmaceutically acceptable salt, solvate, prodrug, and a combination thereof is in a range of 1-100 mg/kg.

The second aspect of the disclosure relates to a gold(III) complex represented by formula (I) or formula (II):

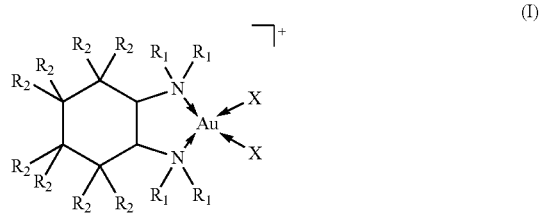

-continued

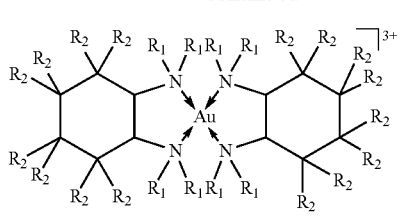

(II)

or a pharmaceutically acceptable salt, solvate, or prodrug thereof;

where each $R_1$ is independently a hydrogen, an optionally substituted $C_1$-$C_8$ alkyl group, or an optionally substituted $C_6$-$C_8$ aryl group;

each $R_2$ is independently a hydrogen, a halogen, a hydroxyl, an amino, a nitro, a cyano, an optionally substituted alkyl, an optionally substituted cycloalkyl, an optionally substituted heterocyclyl, an optionally substituted arylalkyl, an optionally substituted heteroaryl, an optionally substituted alkoxyl, an optionally substituted aryl, an optionally substituted alkenyl, a N-monosubstituted amino group, or a N,N-disubstituted amino group; and X is at least one pharmaceutically acceptable anion such as chloride, bromide, and iodide;

with the proviso that $R_1$ and $R_2$ are not each a hydrogen.

In one embodiment, at least one $R_1$ is an optionally substituted $C_1$-$C_8$ alkyl group.

In one embodiment, at least one $R_2$ is an optionally substituted alkyl group.

In one embodiment, the gold(III) complex represented by formula (I) has X as chloride.

In one embodiment, the gold(III) complex of the second aspect further comprises at least one counterion which is at least one pharmaceutically acceptable anion selected from the group consisting of fluoride, chloride, bromide, iodide, nitrate, sulfate, phosphate, methanesulfonate, ethanesulfonate, p-toluenesulfonate, salicylate, malate, maleate, succinate, tartrate, citrate, acetate, perchlorate, trifluoromethanesulfonate, acetylacetonate, hexafluorophosphate, and hexafluoroacetylacetonate.

In one embodiment, the at least one counterion is chloride.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIG. 8A is a micrograph of classical Hodgkin lymphoma L-540 cells in a cell culture medium without complex 1 and/or complex 2.

FIG. 8B is a micrograph of L-540 cells after a 72-hour treatment with 10 μM of complex 1.

FIG. 8C is a micrograph of L-540 cells after a 72-hour treatment with 25 μM of complex 1.

FIG. 8D is a micrograph of L-540 cells after a 72-hour treatment with 50 μM of complex 1.

FIG. 8E is a micrograph of L-540 cells after a 72-hour treatment with 100 μM of complex 1.

FIG. 8F is a micrograph of L-540 cells after a 72-hour treatment with 10 μM of complex 2.

FIG. 8G is a micrograph of L-540 cells after a 72-hour treatment with 25 μM of complex 2.

FIG. 8H is a micrograph of L-540 cells after a 72-hour treatment with 50 μM of complex 2.

FIG. 8I is a micrograph of L-540 cells after a 72-hour treatment with 100 μM of complex 2.

FIG. 8J is a histogram showing the percentage of living L-540 cells evaluated by a trypan blue dye exclusion assay after a 72-hour treatment with complex 1.

FIG. 9A is a micrograph of ovarian cancer A2780 cells in a cell culture medium without complex 1 and/or complex 2.

FIG. 9B is a micrograph of A2780 cells after a 72-hour treatment with 5 μM of complex 1.

FIG. 9C is a micrograph of A2780 cells after a 72-hour treatment with 5 μM of complex 1.

FIG. 9D is a micrograph of A2780 cells after a 72-hour treatment with 10 μM of complex 1.

FIG. 9E is a micrograph of A2780 cells after a 72-hour treatment with 25 μM of complex 1.

FIG. 9F is a micrograph of A2780 cells after a 72-hour treatment with 5 μM of complex 2.

FIG. 9G is a micrograph of A2780 cells after a 72-hour treatment with 5 μM of complex 2.

FIG. 9H is a micrograph of A2780 cells after a 72-hour treatment with 10 μM of complex 2.

FIG. 9I is a micrograph of A2780 cells after a 72-hour treatment with 25 μM of complex 2.

FIG. 9J is a micrograph of cisplatin-resistant ovarian cancer A2780cis cells in a cell culture medium without complex 1 and/or complex 2.

FIG. 9K is a micrograph of A2780cis cells after a 72-hour treatment with 10 μM of complex 1.

FIG. 9L is a micrograph of A2780cis cells after a 72-hour treatment with 25 μM of complex 1.

FIG. 9M is a micrograph of A2780cis cells after a 72-hour treatment with 50 μM of complex 1.

FIG. 9N is a micrograph of A2780cis cells after a 72-hour treatment with 100 μM of complex 1.

FIG. 9O is a micrograph of A2780cis cells after a 72-hour treatment with 10 μM of complex 2.

FIG. 9P is a micrograph of A2780cis cells after a 72-hour treatment with 25 μM of complex 2.

FIG. 9Q is a micrograph of A2780cis cells after a 72-hour treatment with 50 µM of complex 2.

FIG. 9R is a micrograph of A2780cis cells after a 72-hour treatment with 100 µM of complex 2.

DETAILED DESCRIPTION OF THE EMBODIMENTS

Figure 1:
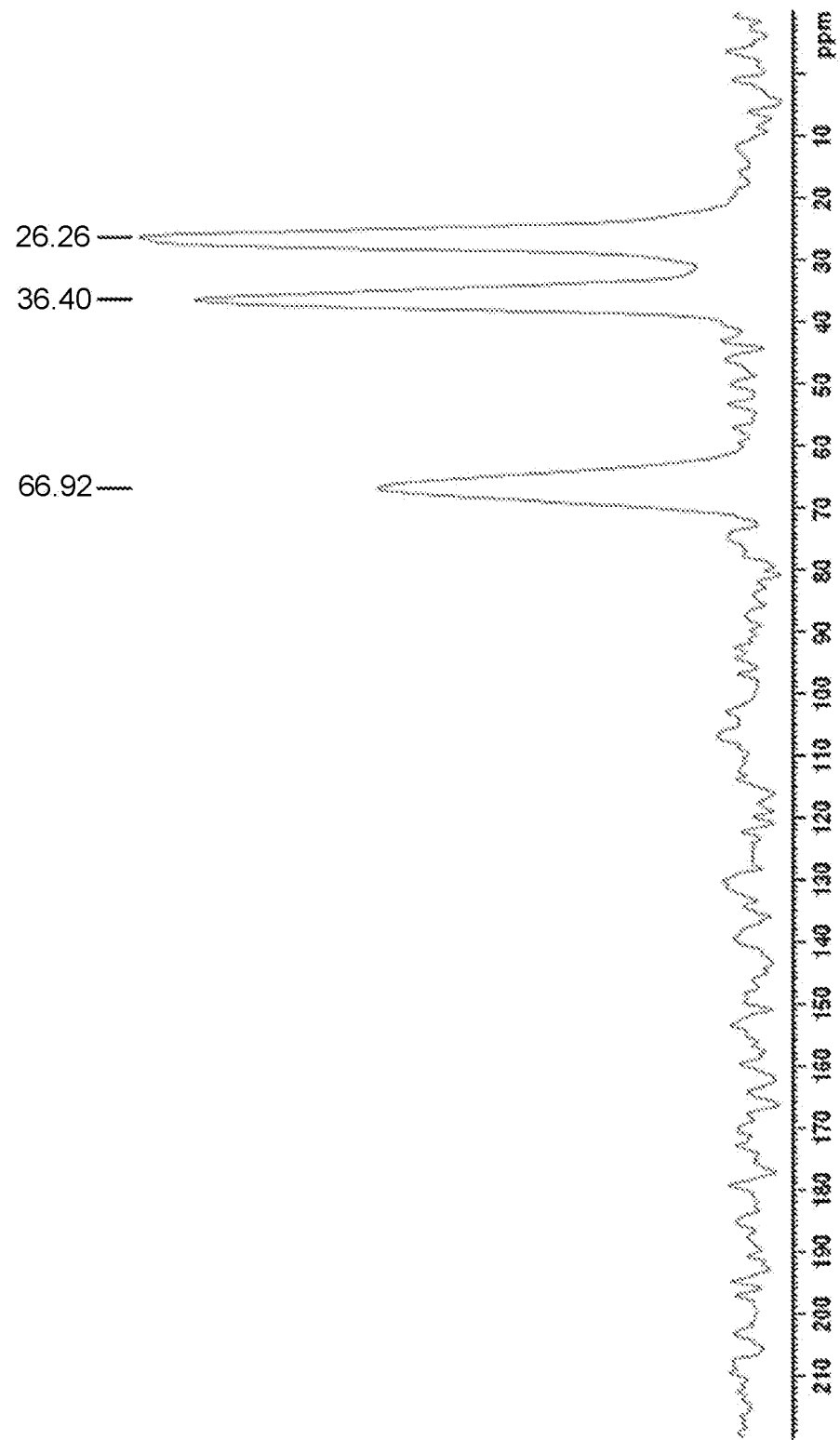
FIG. 1 is a solid-state $^{13}$C spectrum for complex 2 at a spinning rate of 4 kHz.

Embodiments of the present disclosure will now be described more fully hereinafter with reference to the accompanying drawings, in which some, but not all of the embodiments of the disclosure are shown.

The present disclosure will be better understood with reference to the following definitions.

As used herein, the words "a" and "an" and the like carry the meaning of "one or more". Within the description of this disclosure, where a numerical limit or range is stated, the endpoints are included unless stated otherwise. Also, all values and subranges within a numerical limit or range are specifically included as if explicitly written out.

As used herein, "compound" and "complex" are used interchangeably, and are intended to refer to a chemical entity, whether in the solid, liquid or gaseous phase, and whether in a crude mixture or purified and isolated.

The first aspect of the disclosure relates to a method for treating cancer, comprising administering an effective amount of at least one of a gold(III) complex represented by formula (I), a gold(III) complex represented by formula (II):

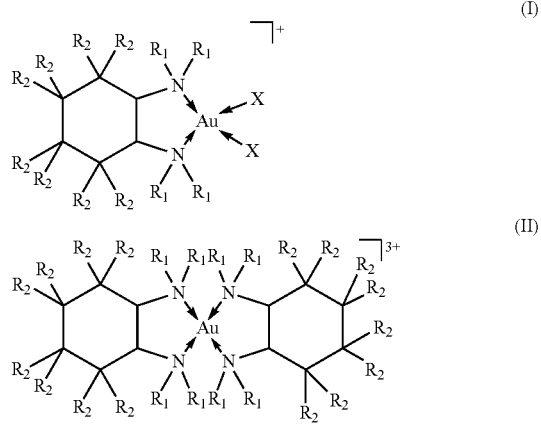

a pharmaceutically acceptable salt, solvate, prodrug, and a combination thereof to a subject, where the cancer may be ovarian cancer, Hodgkin lymphoma, or both, each of $R_1$ may be independently a hydrogen, an optionally substituted $C_1$-$C_8$ alkyl group, or an optionally substituted $C_6$-$C_8$ aryl group, each of $R_2$ may be independently a hydrogen, a halogen, a hydroxyl, an amino, a nitro, a cyano, an optionally substituted alkyl, an optionally substituted cycloalkyl, an optionally substituted heterocyclyl, an optionally substituted arylalkyl, an optionally substituted heteroaryl, an optionally substituted alkoxyl, an optionally substituted aryl, an optionally substituted alkenyl, a N-monosubstituted amino group, or a N,N-disubstituted amino group; and X may be at least one pharmaceutically acceptable anion such as chloride, bromide, or iodide. In one embodiment, the cancer is not prostate cancer, lung cancer, and/or gastric cancer.

The term "alkyl", as used herein, unless otherwise specified, refers to a straight or branched hydrocarbon fragment. Non-limiting examples of such hydrocarbon fragments include methyl, ethyl, propyl, isopropyl, butyl, isobutyl, t-butyl, pentyl, isopentyl, neopentyl, hexyl, isohexyl, 3-methylpentyl, 2,2-dimethylbutyl, and 2,3-dimethylbutyl. As used herein, the term "cycloalkyl" refers to a cyclized alkyl group. Exemplary cycloalkyl groups include, but are not limited to, cyclopropyl, cyclobutyl, cyclopentyl, cyclohexyl, norbornyl, and adamantyl. Branched cycloalkyl groups, for example, 1-methylcyclopropyl and 2-methycyclopropyl groups, are included in the definition of cycloalkyl as used in the present disclosure.

The term "alkenyl" refers to a straight, branched, or cyclic hydrocarbon fragment containing at least one C=C double bond. Exemplary alkenyl groups include, without limitation, 1-propenyl, 2-propenyl (or "allyl"), 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, and 9-decenyl.

The term "aryl", as used herein, and unless otherwise specified, refers to phenyl, biphenyl, naphthyl, anthracenyl, and the like. The term "heteroaryl" refers to an aryl group where at least one carbon atom is replaced with a heteroatom (e.g. nitrogen, oxygen, sulfur) and can be indolyl, furyl, imidazolyl, triazolyl, triazinyl, oxazolyl, isoxazolyl, thiazolyl, isothiazolyl, pyrazolyl, pyrrolyl, pyrazinyl, tetrazolyl, pyridyl (or its N-oxide), thienyl, pyrimidinyl (or its N-oxide), 1H-indolyl, isoquinolyl (or its N-oxide), or quinolyl (or its N-oxide), for example.

As used herein, the term "substituted" refers to at least one hydrogen atom that is replaced with a non-hydrogen group, provided that normal valencies are maintained and that the substitution results in a stable compound. When a compound or a R group is noted as "optionally substituted", the substituents are selected from the exemplary group including, but not limited to, aroyl (as defined hereinafter); halogen (e.g. chlorine, bromine, fluorine or iodine); alkoxy (i.e. straight or branched chain alkoxy having 1 to 10 carbon atoms, and includes, for example, methoxy, ethoxy, propoxy, isopropoxy, butoxy, isobutoxy, sec-butoxy, tert-butoxy, pentoxy, isopentoxy, hexyloxy, heptyloxy, octyloxy, nonyloxy, and decyloxy); cycloalkyloxy including cyclopentyloxy, cyclohexyloxy, and cycloheptyloxy; aryloxy including phenoxy and phenoxy substituted with halogen, alkyl, alkoxy, and haloalkyl (which refers to straight or branched chain alkyl having 1 to 8 carbon atoms which are substituted by at least one halogen, and includes, for example, chloromethyl, bromomethyl, fluoromethyl, iodomethyl, 2-chloroethyl, 2-bromoethyl, 2-fluoroethyl, 3-chloropropyl, 3-bromopropyl, 3-fluoropropyl, 4-chlorobutyl, 4-fluorobutyl, dichloromethyl, dibromomethyl, difluoromethyl, diiodomethyl, 2,2-dichloroethyl, 2,2-dibromoethyl, 2,2-difluoroethyl, 3,3-dichloropropyl, 3,3-difluoropropyl, 4,4-dichlorobutyl, 4,4-difluorobutyl, trichloromethyl, trifluoromethyl, 2,2,2-trifluoroethyl, 2,3,3-trifluoropropyl, 1,1,2,2-tetrafluoroethyl, 2,2,3,3-tetrafluoropropyl); hydrocarbyl; arylalkyl; hydroxy; alkoxy; oxo; alkanoyl; alkanoyloxy; amino; alkylamino;

arylamino; arylalkylamino; disubstituted amines (e.g. in which the two amino substituents are selected from the exemplary group including, but not limited to, alkyl, aryl, or arylalkyl); alkanoylamino; thiol; alkylthio; arylthio; arylalkylthio; alkylthiono; arylthiono; aryalkylthiono; alkylsulfonyl; arylsulfonyl; arylalkylsulfonyl; sulfonamido (e.g. —SO$_2$NH$_2$); substituted sulfonamide; nitro; cyano; carboxy; carbamyl (e.g. —CONH$_2$, —CONHalkyl, —CONHaryl, —CONHarylalkyl or cases where there are two substituents on one nitrogen from alkyl, aryl, or arylalkyl); alkoxycarbonyl; aryl; heteroarylcarbonyl; heterocyclyl; and mixtures thereof and the like. The substituents may be either unprotected, or protected as necessary, as known to those skilled in the art, for example, as taught in Greene, et al., "Protective Groups in Organic Synthesis", John Wiley and Sons, Second Edition, 1991, hereby incorporated by reference in its entirety).

The term "heterocyclyl" as used in this disclosure refers to a 3-8, preferably 4-8, more preferably 4-7 membered monocyclic ring or a fused 8-12 membered bicyclic ring which may be saturated or partially unsaturated, which monocyclic or bicyclic ring contains 1 to 4 heteroatoms selected from oxygen, nitrogen, silicon, or sulfur. Examples of such monocyclic rings include oxaziridinyl, homopiperazinyl, oxiranyl, dioxiranyl, aziridinyl, pyrrolidinyl, azetidinyl, pyrazolidinyl, oxazolidinyl, piperidinyl, piperazinyl, morpholinyl, thiomorpholinyl, thiazolidinyl, hydantoinyl, valerolactamyl, oxiranyl, oxetanyl, dioxolanyl, dioxanyl, oxathiolanyl, oxathianyl, dithianyl, dihydrofuranyl, tetrahydrofuranyl, dihydropyranyl, tetrahydropyranyl, tetrahydropyridyl, tetrahydropyrimidinyl, tetrahydrothiophenyl, tetrahydrothiopyranyl, diazepanyl, and azepanyl. Examples of such bicyclic rings include indolinyl, isoindolinyl, benzopyranyl, quinuclidinyl, 2,3,4,5-tetrahydro-1,3,benzazepine, 4-(benzo-1,3,dioxol-5-methyl)piperazine, and tetrahydroisoquinolinyl. Further, "substituted heterocyclyl" may refer to a heterocyclyl ring which has additional (e.g. one or more) oxygen atoms bonded to the ring atoms of parent heterocylcyl ring. An example of a heterocyclyl substituted with one or more oxygen atoms is 1,1-dioxido-1,3-thiazolidinyl.

The term "alkylthio" as used in this disclosure refers to a divalent sulfur with alkyl occupying one of the valencies and includes the groups methylthio, ethylthio, propylthio, butylthio, pentylthio, hexylthio, and octylthio.

The term "alkanoyl" as used in this disclosure refers to an alkyl group having 2 to 18 carbon atoms that is bound with a double bond to an oxygen atom. Examples of alkanoyl include, acetyl, propionyl, butyryl, isobutyryl, pivaloyl, valeryl, hexanoyl, octanoyl, lauroyl, and stearoyl.

Examples of aroyl are benzoyl and naphthoyl, and "substituted aroyl" may refer to benzoyl or naphthoyl substituted by at least one substituent including those selected from halogen, amino, nitro, hydroxy, alkyl, alkoxy and haloalkyl on the benzene or naphthalene ring.

The term "arylalkyl" as used in this disclosure refers to a straight or branched chain alkyl moiety having 1 to 8 carbon atoms that is substituted by an aryl group or a substituted aryl group having 6 to 12 carbon atoms, and includes benzyl, 2-phenethyl, 2-methylbenzyl, 3-methylbenzyl, 4-methylbenzyl, 2,4-dimethylbenzyl, 2-(4-ethylphenyl)ethyl, 3-(3-propylphenyl)propyl.

The term "heteroarylcarbonyl" as used in this disclosure refers to a heteroaryl moiety with 5 to 10 membered mono- or fused-heteroaromatic ring having at least one heteroatom selected from nitrogen, oxygen and sulfur as mentioned above, and includes, for example, furoyl, nicotinoyl, isonicotinoyl, pyrazolylcarbonyl, imidazolylcarbonyl, pyrimidinylcarbonyl, and benzimidazolyl-carbonyl. Further, "substituted heteroarylcarbonyl" may refer to the above mentioned heteroarylcarbonyl which is substituted by at least one substituent selected from halogen, amino, vitro, hydroxy, alkoxy and haloalkyl on the heteroaryl nucleus, and includes, for example, 2-oxo-1,3-dioxolan-4-ylmethyl, 2-oxo-1,3-dioxan-5-yl.

Vinyl refers to an unsaturated substituent having at least one unsaturated double bond and having the formula CH$_2$═CH—. Accordingly, said "substituted vinyl" may refer to the above vinyl substituent having at least one of the protons on the terminal carbon atom replaced with alkyl, cycloalkyl, cycloalkylalkyl, aryl, substituted aryl, heteroaryl or substituted heteroaryl.

The term "hydrocarbyl" as used herein refers to a univalent hydrocarbon group containing up to about 24 carbon atoms (i.e. a group containing only carbon and hydrogen atoms) and that is devoid of olefinic and acetylenic unsaturation, and includes alkyl, cycloalkyl, alkyl-substituted cycloalkyl, cycloalkyl-substituted cycloalkyl, cycloalkylalkyl, aryl, alkyl-substituted aryl, cycloalkyl-substituted aryl, arylalkyl, alkyl-substituted aralkyl, and cycloalkyl-substituted aralkyl. Further, functionally-substituted hydrocarbyl groups may refer to a hydrocarbyl group that is substituted by one or more functional groups selected from halogen atoms, amino, nitro, hydroxy, hydrocarbyloxy (including alkoxy, cycloalkyloxy, and aryloxy), hydrocarbylthio (including alkylthio, cycloalkylthio, and arylthio), heteroaryl, substituted heteroaryl, alkanoyl, aroyl, substituted aroyl, heteroarylcarbonyl, and substituted heteroarylcarbonyl.

In some embodiments, R$_1$ is hydrogen. In one embodiment, R$_2$ is hydrogen. In another embodiment, X is chloride.

In the gold(III) complex of formula (I), the gold(III) atom may be covalently coordinated to the two vicinal nitrogen atoms on the ligand with a diaminocyclohexane skeletal structure and the two X ligands. In the gold(III) complex of formula (II), the gold(III) atom may be covalently coordinated to the two vicinal nitrogen atoms on each ligand.

In some embodiments, the gold(III) complex represented by formula (I) is

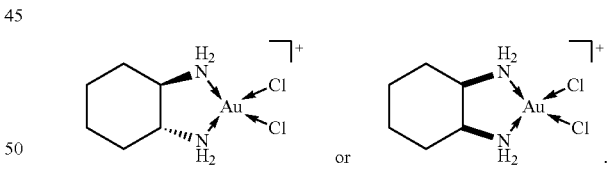

In some embodiments, the gold(III) complex represented by formula (II) is

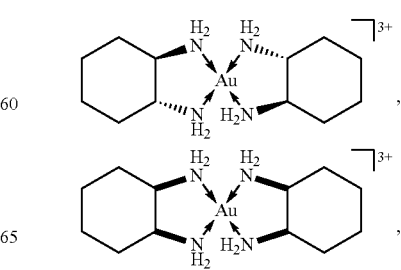

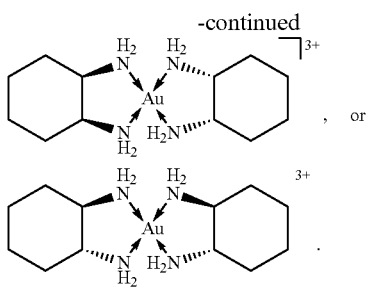

The generally accepted convention for representing stereochemical compounds, which is also adhered to herein, is the following:

a compound represented without stereo bonds, e.g. the cyclohexyl fragment, is racemic or the configuration of the stereogenic center is not defined;

a compound described with one of the descriptors "(±)", "rel", or "rac", is racemic;

a compound represented with solid bars refers to a non-racemic compound and the stereochemistry of the stereogenic centers are relative; and a compound represented with solid and broken wedges but without the descriptors "(±)", "rel", or "rac" refers to a non-racemic or an enantio-enriched compound, where its stereochemistry is absolute.

In most embodiments, the gold(III) complex is administered as a pharmaceutically acceptable salt having at least one counterion. The term "pharmaceutically acceptable salt" refers the gold(III) complex of formula (I) or the gold(III) complex of formula(II) with a counterion. As used herein, the term "counterion" refers to an anion, preferably a pharmaceutically acceptable anion that is associated with the gold(III) complex of formula (I) or the gold(III) complex of formula (II). Non-limiting examples of pharmaceutically acceptable counterions include halides, such as fluoride, chloride, bromide, iodide, nitrate, sulfate, phosphate, amide, methanesulfonate, ethanesulfonate, p-toluenesulfonate, salicylate, malate, maleate, succinate, tartrate, citrate, acetate, perchlorate, trifluoromethanesulfonate (triflate), acetylacetonate, hexafluorophosphate, and hexafluoroacetylacetonate. In some embodiments, the counterion is a halide, preferably chloride.

The phrase "pharmaceutically acceptable" as used herein refers to counterions, compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. Therefore, the composition refers to the combination of an active ingredient with a carrier, inert or active, making the composition especially suitable for diagnostic or therapeutic use in vivo or ex vivo.

As used herein, "derivative" refers to a chemically or biologically modified version of a chemical compound that is structurally similar to a parent compound and (actually or theoretically) derivable from that parent compound. A "derivative" differs from an "analog" in that a parent compound may be the starting material to generate a "derivative", whereas the parent compound may not necessarily be used as the starting material to generate an "analog". A derivative may or may not have different chemical or physical properties of the parent compound. For example, the derivative may be more hydrophilic or it may have altered reactivity compared to the parent compound. Derivatization (i.e. modification) may involve substitution of one or more moieties within the molecule (e.g. a change in functional group). The term "derivative" also includes conjugates, and prodrugs of a parent compound (i.e. chemically modified derivatives which can be converted into the original compound under physiological conditions).

As used herein, the term "analog" refers to a chemical compound that is structurally similar to a parent compound, but differs slightly in composition (e.g. at least one atom or functional group is different, added, or removed). The analog may or may not have different chemical or physical properties than the original compound and may or may not have improved biological and/or chemical activity. For example, the analog may be more hydrophilic or it may have altered reactivity compared to the parent compound. The analog may mimic the chemical and/or biological activity of the parent compound (i.e. it may have similar or identical activity), or, in some cases, may have increased or decreased activity. The analog may be a naturally or non-naturally occurring variant of the original compound. Other types of analogs include isomers (enantiomers, diastereomers, and the like) and other types of chiral variants of a compound, as well as structural isomers.

The term "solvate" means a physical association of the gold(III) complex of formula (I) or the gold(III) complex of formula (II) with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or non-stoichiometric amount of the solvent molecules. Solvate encompasses both solution-phase and isolable solvates. Exemplary solvates include, but are not limited to, hydrates, ethanolates, methanolates, and isopropanolates. Methods of solvation are generally known in the art.

The present disclosure is further intended to include all isotopes of atoms occurring in the present compounds. Isotopes include those atoms having the same atomic number but different mass numbers. By way of general example, and without limitation, isotopes of hydrogen include deuterium and tritium. Isotopes of carbon include $^{13}C$ and $^{14}C$. Isotopically labeled compounds of the disclosure can generally be prepared by conventional techniques known to those skilled in the art or by processes and methods analogous to those described herein, using an appropriate isotopically labeled reagent in place of the non-labeled reagent otherwise employed.

As used herein, the terms "treat", "treatment", and "treating" in the context of the administration of a therapy to a subject in need thereof refer to the reduction or inhibition of the progression and/or duration of a disease (e.g. cancer), the reduction or amelioration of the severity of the disease, and/or the amelioration of one or more symptoms thereof resulting from the administration of one or more therapies. "Treating" or "treatment" of the disease includes preventing the disease from occurring in a subject that may be predisposed to the disease but does not yet experience or exhibit symptoms of the disease (prophylactic treatment), inhibiting the disease (slowing or arresting its development), ameliorating the disease, providing relief from the symptoms or side-effects of the disease (including palliative treatment), and relieving the disease (causing regression of the disease).

With regard to the disease, these terms simply mean that one or more of the symptoms of the disease will be reduced. Such terms may refer to one, two, three, or more results following the administration of one, two, three, or more therapies: (1) a stabilization, reduction (e.g. by more than 10%, 20%, 30%, 40%, 50%, preferably by more than 60% of the population of cancer cells and/or tumor size before administration), or elimination of the cancer cells, (2) inhibiting cancerous cell division and/or cancerous cell proliferation, (3) relieving to some extent (or, preferably, eliminating) one or more symptoms associated with a pathology related to or caused in part by unregulated or aberrant cellular division, (4) an increase in disease-free, relapse-free, progression-free, and/or overall survival, duration, or rate, (5) a decrease in hospitalization rate, (6) a decrease in hospitalization length, (7) eradication, removal, or control of primary, regional and/or metastatic cancer, (8) a stabilization or reduction (e.g. by at least 10%, 20%, 30%, 40%, 50%, 60%, 70%, preferably at least 80% relative to the initial growth rate) in the growth of a tumor or neoplasm, (9) an impairment in the formation of a tumor, (10) a reduction in mortality, (11) an increase in the response rate, the durability of response, or number of patients who respond or are in remission, (12) the size of the tumor is maintained and does not increase or increases by less than 10%, preferably less than 5%, preferably less than 4%, preferably less than 2%, (13) a decrease in the need for surgery (e.g. colectomy, mastectomy), and (14) preventing or reducing (e.g. by more than 10%, more than 30%, preferably by more than 60% of the population of metastasized cancer cells before administration) the metastasis of cancer cells.

The terms "patient", "subject", and "individual" are used interchangeably. As used herein, they refer to individuals suffering from a disease and encompass mammals. None of the terms require that the individual be under the care and/or supervision of a medical professional. Mammals are any member of the mammalian class, including but are not limited to humans, non-human primates, such as chimpanzees, and other apes and monkey species, farm animals, such as cattle, horses, sheep, goats, swine, domestic animals, such as rabbits, dogs, and cats, laboratory animals including rodents, such as rats, mice and guinea pigs, and the like. In preferred embodiments, the subject is a human.

A subject in need of treatment includes a subject already with the disease, a subject which does not yet experience or exhibit symptoms of the disease, and a subject predisposed to the disease. In preferred embodiments, the subject is a person who is predisposed to cancer, e.g. a person with a family history of cancer. Women who have (i) certain inherited genes (e.g. mutated BRCA1 and/or mutated BRCA2), (ii) been taking estrogen alone (without progesterone) after menopause for many years (at least 5, at least 7, or at least 10), and/or (iii) been taking fertility drug clomiphene citrate, are at a higher risk of contracting ovarian cancer. People who have had infectious mononucleosis (an infection caused by the Epstein-Barr virus (EBV)), and/or are infected with HIV (human immunodeficiency virus), are at a higher risk of contracting Hodgkin lymphoma.

In another embodiment, the subject refers to a cancer patient who has been previously administered/treated with cisplatin and have cisplatin resistance (for example in the form of high ERCC1 mRNA levels, overexpression of HER-2/neu, activation of the PI3-K/Akt pathway, loss of p53 function, and/or overexpression of antiapoptotic bcl-2).

The methods for treating cancer and other proliferative disorders described herein inhibit, remove, eradicate, reduce, regress, diminish, arrest or stabilize a cancerous tumor, including at least one of the tumor growth, tumor cell viability, tumor cell division and proliferation, tumor metabolism, blood flow to the tumor and metastasis of the tumor. In some embodiments, the size of a tumor, whether by volume, weight or diameter, is reduced after the treatment by at least 5%, 10%, 15%, 20%, 25%, 30%, 40%, 50%, 60%, 70%, 75%, 80%, 85%, 90%, 95%, 99%, or 100%, relative to the tumor size before treatment. In other embodiments, the size of a tumor after treatment does not reduce but is maintained the same as the tumor size before treatment. Methods of assessing tumor size include but are not limited to CT scan, MRI, DCE-MRI and PET scan.

As used herein, the terms "therapies" and "therapy" can refer to any method, composition, and/or active ingredient that can be used in the treatment and/or management of the disease or one or more symptoms thereof. In some embodiments, the method for treating the disease involves the administration of a unit dosage or a therapeutically effective amount of the active ingredient to a subject in need thereof.

The terms "effective amount", "therapeutically effective amount", or "pharmaceutically effective amount" refer to that amount of the active ingredient being administered which will relieve to some extent one or more of the symptoms of the disease being treated. The result can be reduction and/or alleviation of the signs, symptoms, or causes of a disease, or any other desired alteration of a biological system. For example, an "effective amount" for therapeutic uses is the amount of the gold(III) complex of formula (I), the gold(III) complex of formula (II), the salt thereof, the solvate thereof, the prodrug thereof, or a combination thereof as disclosed herein required to provide a clinically significant decrease in a disease. An appropriate "effective amount" may differ from one individual to another. An appropriate "effective amount" in any individual case may be determined using techniques, such as a dose escalation study.

The dosage and treatment duration are dependent on factors, such as bioavailability of a drug, administration mode, toxicity of a drug, gender, age, lifestyle, body weight, the use of other drugs and dietary supplements, the disease stage, tolerance and resistance of the body to the administered drug, etc., and then determined and adjusted accordingly. In at least one embodiment, the at least one of the gold(III) complex of formula (I), the gold(III) complex of formula (II), the salt thereof, the solvate thereof, the prodrug thereof, and the combination thereof is administered in an effective amount in a range of 1-100 mg/kg based on the weight of the subject, preferably 10-80 mg/kg, more preferably 20-50 mg/kg.

In most embodiments, the gold(III) complex of formula (I), the gold(III) complex of formula(II), the salt thereof, the solvate thereof, the prodrug thereof, or the combination thereof is formulated in a composition. As used herein, a "composition" refers to a mixture of the active ingredient with other chemical components, such as pharmaceutically acceptable carriers and excipients. One purpose of a composition is to facilitate administration of the gold(III) complex of formula (I), the gold(III) complex of formula(II), the salt thereof, the solvate thereof, the prodrug thereof, or a combination thereof to a subject. Depending on the intended mode of administration (oral, parenteral, or topical), the composition can be in the form of solid, semi-solid or liquid dosage forms, such as tablets, suppositories, pills, capsules, powders, liquids, or suspensions, preferably in unit dosage form suitable for single administration of a precise dosage.

The term "active ingredient", as used herein, refers to an ingredient in the composition that is biologically active, for example, the gold(III) complex of formula (I), the gold(III) complex of formula (II), a salt thereof, a prodrug thereof, and a solvate thereof.

In most embodiments, the composition comprises at least 0.5 wt %, 5 wt %, 10 wt %, 15 wt %, 20 wt %, 25 wt %, 30 wt %, 35 wt %, 40 wt %, 45 wt %, 50 wt %, 55 wt %, 60 wt %, 65 wt %, 70 wt %, 75 wt %, 80 wt %, 85 wt %, 90 wt %, 95 wt %, 99 wt %, or 99.9 wt %, of the gold(III) complex of formula (I), the gold(III) complex of formula (II), the pharmaceutically acceptable salt thereof, the pharmaceutically acceptable solvate thereof, or a combination thereof. The composition may comprise 0.01-50 μM, 0.01-30 μM, preferably 0.01-10 μM of the gold(III) complex of formula (I) or the gold(III) complex of formula (II) relative to the total composition. In some embodiments, the composition comprises up to 0.1 wt %, 1 wt %, 5 wt %, or 10 wt % of the pharmaceutically acceptable salt of either the gold(III) complex of formula (I) or the gold(III) complex of formula (II). In some embodiments, the composition comprises up to 0.1 wt %, 1 wt %, 5 wt %, or 10 wt % of the pharmaceutically acceptable solvate thereof of either the gold(III) complex of formula (I) or the gold(III) complex of formula (II). Preferably, the composition may further comprise pharmaceutically acceptable binders, such as sucrose, lactose, xylitol, and pharmaceutically acceptable excipients such as calcium carbonate, calcium phosphate, and dimethyl sulfoxide (DMSO).

The neoplastic activity of the tumor or cancer cells may be localized or initiated in one or more of the following: blood, brain, bladder, lung, cervix, ovary, colon, rectum, pancreas, skin, prostate gland, stomach, intestine, breast, liver, spleen, kidney, head, neck, testicle, bone (including bone marrow), thyroid gland, and central nervous system. Preferably, the composition may be used to treat ovarian cancer and Hodgkin lymphoma such as classical Hodgkin lymphoma and nodular lymphocyte-predominant Hodgkin lymphoma. In some embodiments, the composition is used to treat cisplatin-resistant ovarian cancer and/or classical Hodgkin lymphoma. Therefore, in one embodiment, the subject has ovarian cancer and is currently undergoing, or has completed a cisplatin-based chemotherapy regimen.

In treating certain cancers, the best approach is a combination of surgery, radiotherapy, and/or chemotherapy. Therefore, in at least one embodiment, the composition is employed with radiotherapy. In another embodiment, the composition is employed with surgery. The radiotherapy and/or surgery may be before or after the composition is administered.

In one embodiment, the composition is used for treating cancer and further comprises a second active ingredient, such as a chemotherapeutic agent, for the treatment or prevention of neoplasm, of tumor or cancer cell division, growth, proliferation and/or metastasis in the subject; induction of death or apoptosis of tumor and/or cancer cells; and/or any other form of proliferative disorder. In some embodiments, the first active ingredient is the gold(III) complex of formula (I) and the second active ingredient is the gold(III) complex of formula (II), or vice versa.

Exemplary chemotherapeutic agents include, without limitation, aflibercept, asparaginase, bleomycin, busulfan, carmustine, chlorambucil, cladribine, cyclophosphamide, cytarabine, dacarbazine, daunorubicin, doxorubicin, etoposide, fludarabine, gemcitabine, hydroxyurea, idarubicin, ifosfamide, irinotecan, lomustine, mechlorethamine, melphalan, mercaptopurine, methotrexate, mitomycin, mitoxantrone, pentostatin, procarbazine, topotecan, vinblastine, vincristine, retinoic acid, oxaliplatin, carboplatin, 5-fluorouracil, teniposide, amasacrine, docetaxel, paclitaxel, vinorelbine, bortezomib, clofarabine, capecitabine, actinomycin D, epirubicin, vindesine, methotrexate, 6-thioguanine, tipifarnib, imatinib, erlotinib, sorafenib, sunitinib, dasatinib, nilotinib, lapatinib, gefitinib, temsirolimus, everolimus, rapamycin, bosutinib, pzopanib, axitinib, neratinib, vatalanib, pazopanib, midostaurin, enzastaurin, trastuzumab, cetuximab, panitumumab, rituximab, bevacizumab, mapatumumab, conatumumab, and lexatumumab. The composition may comprise 0.1-50 wt % of the second active ingredient, preferably 10-40 wt %, more preferably 10-20 wt %, relative to the weight of the first active ingredient.

As used herein, a "pharmaceutically acceptable carrier" refers to a carrier or diluent that does not cause significant irritation to an organism, does not abrogate the biological activity and properties of the administered active ingredient, and/or does not interact in a deleterious manner with the other components of the composition in which it is contained. The term "carrier" encompasses any excipient, binder, diluent, filler, salt, buffer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g. Remington's Pharmaceutical Sciences, 21st Edition, ed. University of the Sciences in Philadelphia, Lippincott, Williams & Wilkins, Philadelphia Pa., 2005, which is incorporated herein by reference in its entirety). Examples of physiologically acceptable carriers include buffers such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN® (ICI, Inc.; Bridgewater, N.J.), polyethylene glycol (PEG), and PLURONICS™ (BASF; Florham Park, N.J.). An "excipient" refers to an inert substance added to a composition to further facilitate administration of a compound. Examples, without limitation, of excipients include calcium carbonate, calcium phosphate, various sugars and types of starch, cellulose derivatives, gelatin, vegetable oils, and polyethylene glycols.

The composition thereof may be administered in a single dose or multiple individual divided doses. In some embodiments, the composition is administered at various dosages (e.g. a first dose with an effective amount of 50 mg/kg and a second dose with an effective amount of 10 mg/kg). In some embodiments, the interval of time between the administration of the composition and the administration of one or more additional therapies may be about 1-5 minutes, 1-30 minutes, 30 minutes to 60 minutes, 1 hour, 1-2 hours, 2-6 hours, 2-12 hours, 12-24 hours, 1-2 days, 2 days, 3 days, 4 days, 5 days, 6 days, 7 days, 1 week, 2 weeks, 3 weeks, 4 weeks, 5 weeks, 6 weeks, 7 weeks, 8 weeks, 9 weeks, 10 weeks, 15 weeks, 20 weeks, 26 weeks, 52 weeks, 11-15 weeks, 15-20 weeks, 20-30 weeks, 30-40 weeks, 40-50 weeks, 1 month, 2 months, 3 months, 4 months, 5 months, 6 months, 7 months, 8 months, 9 months, 10 months, 11 months, 12 months, 1 year, 2 years, or any period of time in between. Preferably, the composition is administered once daily for at least 2 days, 5 days, 6 days, or 7 days. In certain embodiments, the composition and one or more additional therapies are administered less than 1 day, 1 week, 2 weeks, 3 weeks, 4 weeks, one month, 2 months, 3 months, 6 months, 1 year, 2 years, or 5 years apart.

The terms "administer", "administering", "administration", and the like, as used herein, refer to the methods that may be used to enable delivery of the active ingredient and/or the composition to the desired site of biological action. Routes or modes of administration are as set forth herein. These methods include, but are not limited to, oral routes, intraduodenal routes, parenteral injection (including intravenous, subcutaneous, intraperitoneal, intramuscular, intravascular, or infusion), topical and rectal administration. Those of ordinary skill in the art are familiar with administration techniques that can be employed with the compounds and methods described herein. In preferred embodiments, the active ingredient and/or the composition described herein are administered orally.

In other embodiments, the composition has various release rates (e.g. controlled release or immediate release). Immediate release refers to the release of an active ingredient substantially immediately upon administration. In another embodiment, immediate release occurs when there is dissolution of an active ingredient within 1-20 minutes after administration. Dissolution can be of all or less than all (e.g. about 70%, about 75%, about 80%, about 85%, about 90%, about 91%, about 92%, about 93%, about 94%, about 95%, about 96%, about 97%, about 98%, about 99%, about 99.5%, 99.9%, or 99.99%) of the active ingredient. In another embodiment, immediate release results in complete or less than complete dissolution within about 1 hour following administration. Dissolution can be in a subject's stomach and/or intestine. In one embodiment, immediate release results in dissolution of an active ingredient within 1-20 minutes after entering the stomach. For example, dissolution of 100% of an active ingredient can occur in the prescribed time. In another embodiment, immediate release results in complete or less than complete dissolution within about 1 hour following rectal administration. In some embodiments, immediate release is through inhalation, such that dissolution occurs in a subject's lungs.

Controlled-release, or sustained-release, refers to the release of an active ingredient from a composition or dosage form in which the active ingredient is released over an extended period of time. In one embodiment, controlled-release results in dissolution of an active ingredient within 20-180 minutes after entering the stomach. In another embodiment, controlled-release occurs when there is dissolution of an active ingredient within 20-180 minutes after being swallowed. In another embodiment, controlled-release occurs when there is dissolution of an active ingredient within 20-180 minutes after entering the intestine. In another embodiment, controlled-release results in substantially complete dissolution after at least 1 hour following administration. In another embodiment, controlled-release results in substantially complete dissolution after at least 1 hour following oral administration. In another embodiment, controlled-release results in substantially complete dissolution after at least 1 hour following rectal administration. In one embodiment, the composition is not a controlled-release composition.

Solid dosage forms for oral administration can include capsules, tablets, pills, powders, and granules. In such solid dosage forms, the active ingredient is ordinarily combined with one or more adjuvants appropriate to the indicated route of administration. If administered per os, the active ingredient can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering ingredients such as sodium citrate, magnesium or calcium carbonate or bicarbonate. Tablets and pills can additionally be prepared with enteric coatings.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting ingredients, emulsifying and suspending ingredients, and sweetening, flavoring, and perfuming ingredients.

For therapeutic purposes, formulations for parenteral administration can be in the form of aqueous or non-aqueous isotonic sterile injection solutions or suspensions. The term "parenteral", as used herein, includes intravenous, intravesical, intraperitoneal, subcutaneous, intramuscular, intralesional, intracranial, intrapulmonal, intracardial, intrasternal, and sublingual injections, or infusion techniques. These solutions and suspensions can be prepared from sterile powders or granules having one or more of the carriers or diluents mentioned for use in the formulations for oral administration. The active ingredient can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Injectable preparations, for example, sterile injectable aqueous or oleaginous suspensions can be formulated according to the known art using suitable dispersing or wetting ingredients and suspending ingredients. The sterile injectable preparation can also be a sterile injectable solution or suspension in a non-toxic parenterally acceptable diluent or solvent, for example, as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or diglycerides. In addition, fatty acids, such as oleic acid, find use in the preparation of injectables. Dimethyl acetamide, surfactants including ionic and non-ionic detergents, polyethylene glycols can be used. Mixtures of solvents and wetting ingredients such as those discussed above are also useful.

Suppositories for rectal administration can be prepared by mixing the active ingredient with a suitable non-irritating excipient, such as cocoa butter, synthetic mono-, di-, or triglycerides, fatty acids, and polyethylene glycols that are solid at ordinary temperatures but liquid at the rectal temperature and will therefore melt in the rectum and release the drug.

Topical administration can also involve the use of transdermal administration such as transdermal patches or iontophoresis devices. Formulation of drugs is discussed in, for example, Hoover, John E., Remington's Pharmaceutical Sciences, Mack Publishing Co., Easton, Pa., 1975. Another example of includes Liberman, H. A. and Lachman, L., Eds., Pharmaceutical Dosage Forms, Marcel Decker, New York, N.Y., 1980, which is incorporated herein by reference in its entirety).

In one embodiment, the $IC_{50}$ of the gold(III) complexes of formula (I) or formula (II) is in a range of 0.01-100 μM, 1-100 μM, 10-90 μM, 20-80 μM, 30-80 μM, 40-80 μM, 50-80 μM, or 50-75 μM. As used herein, the term "$IC_{50}$" refers to a concentration of the gold(III) complex of formula (I), the gold(III) complex of formula (II), the salt thereof, the prodrug thereof, or the solvate thereof, which causes the death of 50% of cancer cells in 72 hours (3 days).

The $IC_{50}$ can be determined by standard cell viability assays, such as, without limitation, ATP test, Calcein AM assay, clonogenic assay, ethidium homodimer assay, Evans blue assay, Fluorescein diacetate hydrolysis/propidium iodide staining assay, flow cytometry assay, formazan-based assays (MTT, XTT), green fluorescent protein assay, lactate dehydrogenase assay, methyl violet assay, propidium iodide assay, Resazurin assay, Trypan Blue assay and TUNEL assay. Preferably, a MTT assay and/or a Trypan Blue assay is used.

In at least one embodiment, the human cancer cells are derived from commercial cell lines, including but are not limited to HeLa cervical cancer cells, A549 lung cancer cells, HCT15 colon cancer cells, HCT8 or HRT8 colon cancer cells, HCT116 colon cancer cells, DLD1 colon cancer cells, MCF7 breast cancer cells, MDA-MB231 breast cancer cells, A2780 ovarian cancer cells, HePG2 liver cancer cells, L540 Hodgkin lymphoma cells, and DU145 prostatic cancer cells. In some embodiments, cisplatin-resistant cancer cells are used. These cells may be cultured with low doses of cisplatin in order to build resistance to cisplatin while maintaining cell viability. Examples of cisplatin-resistant cancer cells include, but are not limited to, A2780cis cisplatin-resistant ovarian cancer cells and SGC7901cis cisplatin-resistant gastrointestinal cancer cells. In other embodiments, the human cancer cells are cancer cells of a human patient who has been diagnosed with, is suspected of having, or is susceptible to or at risk of having at least one form of cancer, preferably ovarian cancer.

In most embodiments, the method further comprises measuring a concentration of a biomarker and/or detecting a mutation in a biomarker before and/or after the composition is administered. As used herein, the term "biomarker" refers to a characteristic that is objectively measured and evaluated as an indicator of normal biological processes, pathogenic processes or pharmacological responses to a therapeutic intervention. Exemplary cancer biomarkers for ovarian cancer and/or Hodgkin lymphoma include, without limitation, BRCA1, BRCA2, CCL17, CD163, CD30, NF-κB, Gal-1, CA125 HE4 mesothelin, transthyretin, ApoA1, VCAM, IL-6, IL-8, B7-H4, serum amyloid A, transferrin, osteopontin, kallikreins, OVX1, VEGF, AGR-2, inhibin, M-CSF, uPAR, EGF receptor, lysophosphatidyl acid, beta2-microglobulin, miRNA, and Epstein-Barr virus (EBV) DNA. Specifically, potentially predictive cancer biomarkers include, without limitation, mutations in genes BRCA1 and BRCA2 for ovarian cancer.

Cancer biomarkers may be useful in determining the aggressiveness of an identified cancer as well as its likelihood of responding to the treatment. Examples of such prognostic biomarkers include, without limitation, CA125, beta2-microglobulin, and EBV DNA.

The mutation in the biomarker may be detected with a polymerase chain reaction (PCR) assay, DNA microarray, multiplex ligation-dependent probe amplification (MLPA), single strand conformational polymorphism (SSCP), denaturing gradient gel electrophoresis (DGGE), heteroduplex analysis, and restriction fragment length polymorphism (RFLP). The procedures to detect the mutation are well-known to those of ordinary skill in the art.

The concentration of the biomarker may be measured with an assay, for example an antibody-based method (e.g. an ELISA).

As used herein, the term "antibody-based method" refers to any method with the use of an antibody including, but not limited to, enzyme-linked immunosorbent assay (ELISA), Western blotting, immunoprecipitation (IP), enzyme linked immunospot (ELISPOT), immunostaining, immunohistochemistry, immunocytochemistry, affinity chromatography, and the like.

Preferably, an ELISA is used. The term "ELISA" refers to a method of detecting the presence and concentration of a biomarker in a sample. There are several variants of ELISA, including, but not limited to, sandwich ELISA, competitive ELISA, indirect ELISA, ELISA reverse, and the like. The ELISA assay may be a singleplex assay or a multiplex assay, which refers to a type of assay that simultaneously measures multiple analytes in a single run/cycle of the assay. Preferably, a sandwich ELISA is used.

The protocol for measuring the concentration of the biomarker and/or detecting the mutation in the biomarker is known to those of ordinary skill, for example by performing the steps outlined in the commercially available assay kit sold by Sigma-Aldrich, Thermo Fisher Scientific, R & D Systems, ZeptoMetrix Inc., Cayman Inc., Abcam, Trevigen, Dojindo Molecular Technologies, Biovision, and Enzo Life Sciences.

The term "sample" includes any biological sample taken from the subject including a cell, tissue sample, or body fluid. For example, a sample may include a skin sample, a cheek cell sample, saliva, or blood cells. A sample can include, without limitation, a single cell, multiple cells, fragments of cells, an aliquot of a body fluid, whole blood, platelets, serum, plasma, red blood cells, white blood cells, endothelial cells, tissue biopsies, synovial fluid, and lymphatic fluid. In some embodiments, the sample is taken from a tumor.

In some embodiments, the concentration of the biomarker is measured before and after the administration. When the concentration of the biomarker is maintained, the method may further comprise increasing the effective amount of at least one of the gold(III) complex of formula (I), the gold(III) complex of formula (II), the salt thereof, the solvate thereof, the prodrug thereof, and the combination thereof by at least 5%, at least 10%, or at least 30%, up to 50%, up to 60%, or up to 80% of an initial effective amount that is in a range of 1-100 mg/kg based on the weight of the subject. The increased effective amount may be in a range of 1.05-180 mg/kg, preferably 15-140 mg/kg, more preferably 25-90 mg/kg. The subject may be administered with the increased dosage for a longer period (e.g. 1 week more, 2 weeks more, or 2 months more) than the duration with the initial effective amount.

In some embodiments, the mutation in the biomarker is detected before administrating the composition to identify subjects predisposed to the disease. For example, women with a BRCA1 germline mutation are at a higher risk of contracting ovarian cancer.

In some embodiments, the biomarkers are measured/detected after each administration. For example, the measurement may be 1-5 minutes, 1-30 minutes, 30-60 minutes, 1-2 hours, 2-12 hours, 12-24 hours, 1-2 days, 1-15 weeks, 15-20 weeks, 20-30 weeks, 30-40 weeks, 40-50 weeks, 1 year, 2 years, or any period of time in between after the administration.

In some embodiments, the administration is stopped once the subject is treated.

The second aspect of the disclosure relates to a gold(III) complex represented by formula (I) or formula (II):

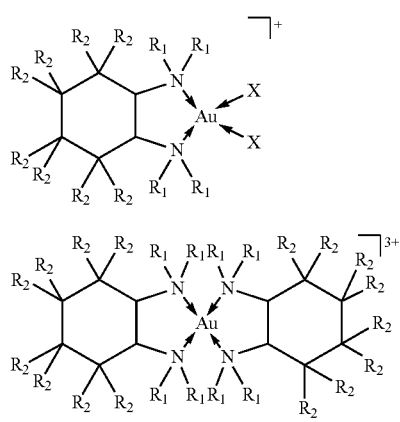

where each of $R_1$ may independently be a hydrogen, an optionally substituted $C_1$-$C_8$ alkyl group, or an optionally substituted $C_6$-$C_8$ aryl group, each of $R_2$ may independently be a hydrogen, a halogen, a hydroxyl, an amino, a nitro, a cyano, an optionally substituted alkyl, an optionally substituted cycloalkyl, an optionally substituted heterocyclyl, an optionally substituted arylalkyl, an optionally substituted heteroaryl, an optionally substituted alkoxyl, an optionally substituted aryl, an optionally substituted alkenyl, a N-monosubstituted amino group, or a N,N-disubstituted amino group, and X may be at least one pharmaceutically acceptable anion such as chloride, bromide, and iodide, with the proviso that $R_1$ and $R_2$ are not each a hydrogen.

In some embodiments, at least one $R_1$ is an optionally substituted $C_1$-$C_8$ alkyl group. For example, at least one $R_1$ is a methyl group and the remaining $R_1$ that are not methyl groups are each a hydrogen atom. Further, there may be one methyl group and a hydrogen atom on each nitrogen atom of the amino group. In one embodiment, at least one $R_2$ is an optionally substituted alkyl group. For example, at least one $R_2$ is a methyl group and the remaining $R_2$ that are not methyl groups are each a hydrogen atom. Further, there may be one methyl group in each cyclohexyl. In a preferred embodiment, X is chloride.

In most embodiments, the gold(III) complex is in the form of the pharmaceutical acceptable salt having at least one counterion which is at least one pharmaceutically acceptable anion selected from the group consisting of fluoride, chloride, bromide, iodide, nitrate, sulfate, phosphate, methanesulfonate, ethanesulfonate, p-toluenesulfonate, salicylate, malate, maleate, succinate, tartrate, citrate, acetate, perchlorate, trifluoromethanesulfonate, acetylacetonate, hexafluorophosphate, and hexafluoroacetylacetonate. Preferably, the counterion is chloride.

The gold(III) complex represented by formula (I) or formula (II) may be prepared by mixing a gold(III) precursor with a ligand of the following formula:

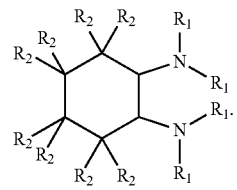

Exemplary gold(III) precursors include, without limitation, sodium tetrachloroaurate(III), potassium tetrachloroaurate(III), cesium tetrachloroaurate(III), sodium tetrabromoaurate(III), potassium tetrabromoaurate(III), caesium tetrabromoaurate(III), and hydrates thereof. The gold(III) precursor and the ligand (for example (1R,2R)-(−)-1,2-diaminocyclohexane) may be dissolved separately in a solvent to form a gold(III) precursor solution and a ligand solution. A concentration of the gold(III) precursor solution and/or the ligand solution may be in a range of 0.005-1 M, 0.01-0.5 M, or 0.01-0.1 M. In some embodiments, the molar ratio of the gold(III) precursor to the ligand is in a range of 1:0.9 to 1:1.1, 1:0.95 to 1:1.05, or 1:0.99 to 1:1.01 to prepare the gold(III) complex of formula (I). In some embodiments, the molar ratio of the gold(III) precursor to the ligand is in a range of 1:1.9 to 1:2.1, 1:1.95 to 1:2.05, or 1:1.99 to 1:2.01 to prepare the gold(III) complex of formula (II). The ligand solution may be added dropwise (or at a rate of 0.05-0.5 ml/min, 0.05-0.3 ml/min, or 0.05-0.1 ml/min) to the gold (III) precursor solution to form a reaction mixture. The reaction mixture may be shaken/stirred throughout the duration of the reaction by employing a rotary shaker, a magnetic stirrer, or an overhead stirrer. In another embodiment, the reaction mixture is left to stand (i.e. not stirred). In one embodiment, the reaction mixture is preferably mixed in a centrifugal mixer with a rotational speed of at least 500 rpm, preferably at least 800 rpm, more preferably at least 1,000 rpm, even though it can also be mixed with a spatula. In one embodiment, the reaction mixture is sonicated. A clear solution may form and may be cooled at a temperature in a range of 0-10° C., 0-6° C., or 0-4° C., for 1-10 days, 1-5 days, or 1-3 days. The solution may be cooled with an external cooling source such as an ice bath with or without salt, a thermostatted thermocirculator, or by refrigerating the solution. Crystallization of the gold(III) complex of formula (I) or formula (II) may occur and the crystals may be collected using methods known to those skilled in the art such as filtration.

As used herein, the term "solvent" includes, but is not limited to, water (e.g. tap water, distilled water, doubly distilled water, deionized water, deionized distilled water), organic solvents, such as ethers (e.g. diethyl ether, tetrahydrofuran, 1,4-dioxane, tetrahydropyran, t-butyl methyl ether, cyclopentyl methyl ether, di-iso-propyl ether), glycol ethers (e.g. 1,2-dimethoxyethane, diglyme, triglyme), alcohols (e.g. methanol, ethanol, trifluoroethanol, n-propanol, i-propanol, n-butanol, i-butanol, t-butanol, n-pentanol, i-pentanol, 2-methyl-2-butanol, 2-trifluoromethyl-2-propanol, 2,3-dimethyl-2-butanol, 3-pentanol, 3-methyl-3-pentanol, 2-methyl-3-pentanol, 2-methyl-2-pentanol, 2,3-dimethyl-3-pentanol, 3-ethyl-3-pentanol, 2-methyl-2-hexanol, 3-hexanol, cyclopropylmethanol, cyclopropanol, cyclobutanol, cyclopentanol, cyclohexanol), aromatic solvents (e.g. benzene, o-xylene, m-xylene, p-xylene, and mixtures of xylenes, toluene, mesitylene, anisole, 1,2-dimethoxybenzene, α,α,α,-trifluoromethylbenzene, fluorobenzene), chlorinated solvents (e.g. chlorobenzene, dichloromethane, 1,2- dichloroethane, 1,1-dichloroethane, chloroform), ester solvents (e.g. ethyl acetate, propyl acetate), amide solvents (e.g. dimethylformamide, dimethylacetamide, N-methyl-2-pyrrolidone), urea solvents, ketones (e.g. acetone, butanone), acetonitrile, propionitrile, butyronitrile, benzonitrile, dimethyl sulfoxide, ethylene carbonate, propylene carbonate, 1,3-dimethyl-3,4,5,6-tetrahydro-2(1H)-pyrimidinone, and mixtures thereof. Preferably, the solvent is absolute ethanol.

Having generally described this disclosure, a further understanding can be obtained by reference to certain specific examples which are provided herein for purposes of illustration only and are not intended to be limiting unless otherwise specified.

EXAMPLE 1

Chemicals

Sodium tetrachloroaurate(III) dihydrate, (1R,2R)-(−)-1,2-diaminocyclohexane (DACH), and glutathione (GSH) were obtained from Sigma-Aldrich, USA. Absolute ethanol was obtained from Merck, $D_2O$ was purchased from Alfa Aesar, and deionized water with a resistivity of 18.6 MΩ/cm$^{-1}$ for solution preparation was obtained directly from a PURELABs Ultra Laboratory Water Purification System.

EXAMPLE 2

Synthesis of Complexes 1(R),2(R)-[Au(DACH) AuCl$_2$]Cl (1) and 1(R),2(R)-[Au(DACH)$_2$Au]Cl$_3$ (2)

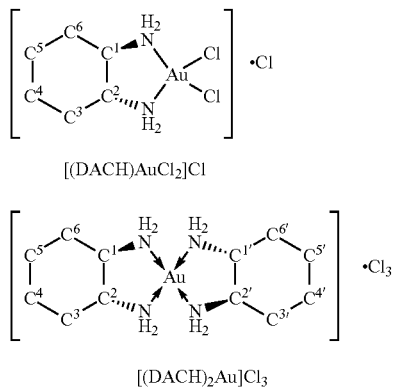

1(R),2(R)-[(DACH)AuCl$_2$]Cl (1) was synthesized by the direct mixing of 200 mg (0.5 mmol) of NaAuCl$_4$.2H$_2$O with 57 mg (0.5 mmol) of (1R,2R)-(−)-1,2-Diaminocyclohexane ligand in alcoholic media as previously described (S. S. Al-Jaroudi, M. Fettouhi, M. I. M. Wazeer, A. A. Isab, and S. Altuwaijri, *Polyhedron*, vol. 50, no. 1, pp. 434-442, 2013, incorporated herein by reference in its entirety). First, 200 mg (0.5 mmol) NaAuCl$_4$.2H$_2$O was dissolved using absolute ethanol, 57 mg (0.5 mmol) of 1(R), 2(R)-DACH was dissolved in absolute ethanol in a separate beaker, and the second solution was then added dropwise with gentle stirring to the first solution. After a clear solution was obtained, the solution was maintained under refrigeration, and after a few days, yellow crystals were collected and used for single crystal X-ray diffraction and elemental analysis (Table 4).

1(R),2(R)-[(DACH)$_2$Au]Cl$_3$ (2) was synthesized by directly mixing one equivalent of Na[AuCl$_4$].2H$_2$O with two equivalents of diamine ligand in alcoholic media using a previously described method (S. S. Al-Jaroudi, M. Monim-ul-Mehboob, M. Altaf, M. Fettouhi, M. I. M. Wazeer, S. Altuwaijri, and A. A. Isab, *New J. Chem.*, vol. 38, no. 7, pp. 3199-3211, 2014, incorporated herein by reference in its entirety). First, 200 mg (0.5 mmol) of NaAuCl$_4$.2H$_2$O was dissolved in absolute ethanol, 114 mg (1.0 mmol) of 1(R), 2(R)-DACH was dissolved in absolute ethanol in a separate beaker, and the second solution was then added dropwise with gentle stirring to the first solution. The white crystals that formed were collected, washed, and used for single crystal X-ray diffraction and elemental analysis (Table 4).

TABLE 1

Elemental data and melting points for the synthesized complexes

| Complex | Melting point (° C.) | Found (Calc.) % | | |
|---|---|---|---|---|
| | | H | C | N |
| (1) | 172 decomp. | 4.02(3.97) | 16.4(15.88) | 6.47(6.17) |
| (2) | 176 decomp. | 5.24(5.96) | 24.75(23.85) | 9.57(9.27) |

EXAMPLE 3

Solution NMR Measurements

All NMR measurements were performed using a JEOL JNM-LA 500 NMR spectrometer. The $^{13}C$ NMR resonance spectra were obtained with $^1H$ broadband decoupling at a frequency of 125.65 MHz, and the peaks were referenced relative to TMS. The spectral conditions were 32 k data points, 0.963 s acquisition time, 1.00 s pulse delay, and a 45° pulse angle. The proton NMR spectra were obtained at a frequency of 500.00 MHz. The $^1H$ and $^{13}C$ NMR chemical shifts of free ligand and both complexes are given in Tables 1 and 2.

TABLE 2

$^1H$ NMR for the synthesized gold(III) complexes and free (1R,2R)-(−)-1,2-diaminocyclohexane in $D_2O$ solvent

| | $^1H$ (δ in ppm) | | | | |
|---|---|---|---|---|---|
| Compound | H1,H2 | H3,H6 (eq) | H3,H6 (ax) | H4,H5 (eq) | H4,H5 (ax) |
| 1(R),2(R)-DACH | 2.19 m | 1.69 m | 1.54 m | 1.13 m | 0.99 m |
| (1) | 2.97 m | 2.07 m | 1.54 m | 1.36 m | 1.04 m |
| (2) | 3.02 m | 2.12 m | 1.55 m | 1.47 m | 1.09 m | m: multiplet

TABLE 3

$^{13}C$ NMR for the synthesized gold(III) complexes and free (1R,2R)-(−)-1,2-diaminocyclohexane in $D_2O$ solvent

| | $^{13}C$ (δ in ppm) | | |
|---|---|---|---|
| Compound | C1,C2 | C3,C6 | C4,C5 |
| 1(R),2(R)-DACH | 56.8 | 34.1 | 25.4 |
| (1) | 65.6 | 33.0 | 23.9 |
| (2) | 64.3 | 32.8 | 23.9 |

For both complexes 1 and 2, Tables 1 and 2 clearly show that the observed number of $^1$H and $^{13}$C resonances was half of the expected number, which might indicate the presence of a $C_2$ center of symmetry. All cyclohexyl protons showed a downfield shift relative to the free diaminocyclohexane ligand. At room temperature, the cyclohexyl ring behaves as a rigid conformer that allows axial and equatorial protons in the cyclohexyl rings in 1 and 2 to be distinguished upon complexation compared with the free diaminocyclohexane. These observed shifts can be explained by the donation of nitrogen lone pairs to the d orbitals of the gold(III) center. This donation caused the nitrogen atoms to be more electron-deficient and made the H1 and H2 protons of the cyclohexyl ring more deshielded, thereby shifting their resonances downfield, indicating that coordination took place through the nitrogen atoms. The resonances for other protons were shifted downfield for the same reason. The observed resonances for the complexes 1 and 2 are different. This variation is due to their different geometries.

Similar downfield shifts were observed for the $^{13}$C resonances of C1 and C2 adjacent to their amino groups. These two carbons become deshielded due to coordination through nitrogen atoms, and the other carbons are shifted upfield.

EXAMPLE 4

Solid-state NMR Measurements

Solid-state $^{13}$C NMR spectra were recorded at 100.613 MHz on a Broker 400 MHz spectrometer at an ambient temperature of 298 K. Samples were packed into 4-mm zirconium oxide (ZrO) rotors. Cross-polarization and high-power decoupling were employed. A pulse delay of 7.0 s and a contact time of 5.0 ms were used in the CPMAS experiments. The magic angle spinning (MAS) rates were maintained at 4 kHz. Carbon chemical shifts were referenced to tetramethylsilane (TMS) by setting the high-frequency isotropic peak of solid adamantane to 38.56 ppm. The solid-state NMR data is given in Table 3.

TABLE 4

Solid-state NMR for synthesized gold(III) complexes

| Compound | C1,C2 | C3,C6 | C4,C5 |
|---|---|---|---|
| (1) | 68.5 | 36.9 | 26.5 |
| (2) | 66.9 | 36.4 | 26.3 |

In the solid state $^{13}$C NMR spectra, significant deshielding was observed (as shown in FIG. 1) for complex 2. A similar trend was observed in the chemical shifts of complex 1, shown in Table 3. This observation shows that the complexes are stable in solution as well as in the solid state.

EXAMPLE 5

IR and Far-IR Spectroscopy

A PerkinElmer FTIR 180 spectrophotometer was used to collect IR spectra for the ligands and synthesized gold(III) complexes within the range of 4000-400 cm$^{-1}$. Far-infrared spectra were recorded for the synthesized complexes 1 and 2 at room temperature with 4 cm$^{-1}$ resolution using polyethylene disks with a far-IR beam splitter.

Both complexes 1 and 2 showed significant N—H stretching vibrations, with an observed blueshift relative to the free ligand within the range of 3200-3500 cm$^{-1}$. This is due to coordination through an N atom and a formation of a five-membered ring with gold(III), which reduces H bonding compared with free amino groups in free DACH.

The far-IR spectrum of complex 1 shows a clear vibration band at 367 cm$^{-1}$, which is assigned to Au—Cl stretching vibration, with another band at 393 cm$^{-1}$ for the Au—N bond (S. S. Al-Jaroudi, M. Fettouhi, M. I. M. Wazeer, A. A. Isab and S. Altuwaijri, *Polyhedron*, vol. 50, pp. 434-442, 2013, incorporated herein by reference in its entirety). Complex 2 lacked symmetric Cl—Au—Cl stretching vibrations at 352 and 367 cm$^{-1}$.

EXAMPLE 6

X-ray Crystallography

Suitable crystals of complexes 1 and 2 were obtained as pale yellow blocks and colorless rods, respectively, from absolute ethanol. The intensity data of the complexes were collected at 173K (−100° C.) on a Stoe Mark II-Image Plate Diffraction System equipped with a two-circle goniometer and using Mo-Kα graphite monochromated radiation (λ=0.71073 A) (Stoe & Cie. (2009). *X-Area & X-RED*32. Stoe & Cie GmbH, Darmstadt, Germany, incorporated herein by reference in its entirety). The structure was solved by direct methods with SHELXS-2014 (G. M. Sheldrick, Acta Cryst. A64, pp. 112-122, 2008, incorporated herein by reference in its entirety). The refinement and all further calculations were carried out with SHELXL-2014. The H atoms from water were located on difference Fourier maps and refined using the distance restraint of O—H=0.84(2) Å and with $U_{iso}$(H)=1.5 $U_{eq}$(O). It was not possible to locate both H atoms on water molecules, O7W and O8W, for complex 2.

The N- and C-bound H-atoms were included in the calculated positions and treated as riding atoms: N—H=0.91 Å and C—H=0.99-1.00 Å with $U_{iso}$(H)=1.2 $U_{eq}$(N,C). The non-H atoms were refined anisotropically using weighted full-matrix least-squares on $F^2$. A semi-empirical absorption correction was applied using the MULscanABS routine in PLATON (A. L. Spek, Acta Cryst. D65, pp. 148-155, 2009, incorporated herein by reference in its entirety). FIGS. 3-7 showing the crystal structures and crystal packing were drawn using Mercury software (C. F. Macrae, I. J. Bruno, J. A. Chisholm, P. R. Edgington, P. McCabe, E. Pidcock, L. Rodriguez-Monge, R. Taylor, J. van de Streek and P. A. Wood, J. Appl. Cryst. 41, pp. 466-470, (2008), incorporated herein by reference in its entirety). The summary of crystallographic data of complexes 1 and 2 is given in Table 6.

TABLE 6

Crystal data and structure refinement details for complexes 1 and 2

| | Complex | |
|---|---|---|
| | 1 | 2 |
| CCDC deposit no. | 1055595 | 1055495 |
| Chemical formula | 2[C$_6$H$_{14}$N$_2$AuCl$_2$]$^+$•2Cl$^-$•H$_2$O | [(C$_6$H$_{14}$N$_2$)$_2$Au]$^{3+}$•3(Cl)$^-$•4(H$_2$O) |
| Molecular weight | 853.03 | 603.76 |
| Crystal system, space group | Monoclinic, P2$_1$ | Monoclinic, P2$_1$ |
| Temperature (K) | 173 | 173 |
| a, b, c (Å) | 9.5692 (5), 8.5645 (5), 14.3950 (8) | 7.4766 (3), 27.3859 (10), 10.7744 (5) |
| β (°) | 95.369 (4) | 90.913 (4) |
| V (Å$^3$) | 1174.57 (11) | 2205.81 (16) |
| Z | 2 | 4 |
| Radiation type | Mo Kα | Mo Kα |
| μ (mm−1) | 13.17 | 7.06 |
| Crystal size (mm) | 0.40 × 0.38 × 0.35 | 0.45 × 0.35 × 0.30 |
| Diffractometer | STOE IPDS 2 diffractometer | STOE IPDS 2 diffractometer |
| Absorption correction | Multi-scan (MULscanABS in PLATON; Spek, 2009) | Multi-scan (MULscanABS in PLATON; Spek, 2009) |
| T$_{min}$, T$_{max}$ | 0.251, 1.000 | 0.448, 1.000 |
| No. of measured, independent and observed [I > 2σ(I)] reflections | 16303, 4442, 4214 | 30420, 8309, 7854 |
| R$_{int}$ | 0.142 | 0.079 |
| (sin θ/λ)$_{max}$ (Å−1) | 0.609 | 0.609 |
| R[F2 > 2σ(F2)], wR(F2), S | 0.045, 0.117, 1.01 | 0.021, 0.043, 0.94 |
| No. of reflections | 4442 | 8309 |
| No. of parameters | 179 | 470 |
| No. of restraints | 1 | 21 |
| Largest diff. peak and hole (e Å$^{-3}$) Δρ$_{max}$, Δρ$_{min}$ (e Å$^{-3}$) | 1.65, −2.38 | 1.08, −1.27 |
| Absolute structural parameter | 1.08, −1.27 | −0.018 (4) |

Figure 3:
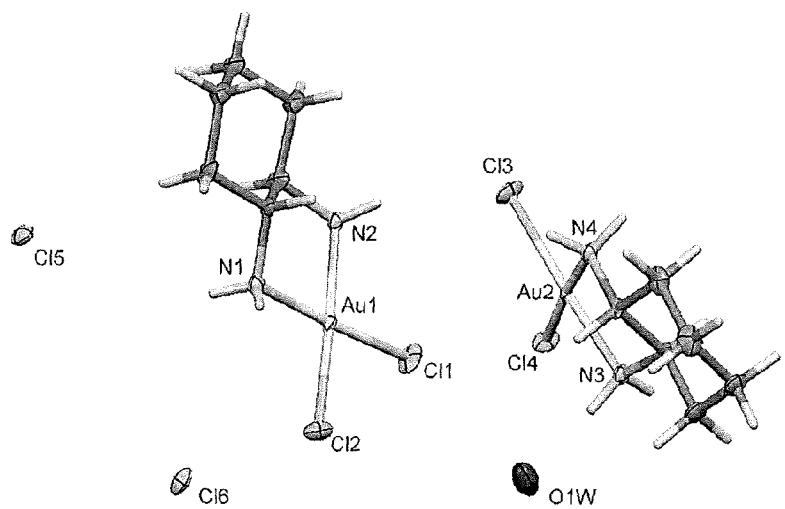
FIG. 3 is a view of the molecular structure of complex 1 with labelled atoms, and the displacement ellipsoids are drawn at the 50% probability level.
Figure 4:
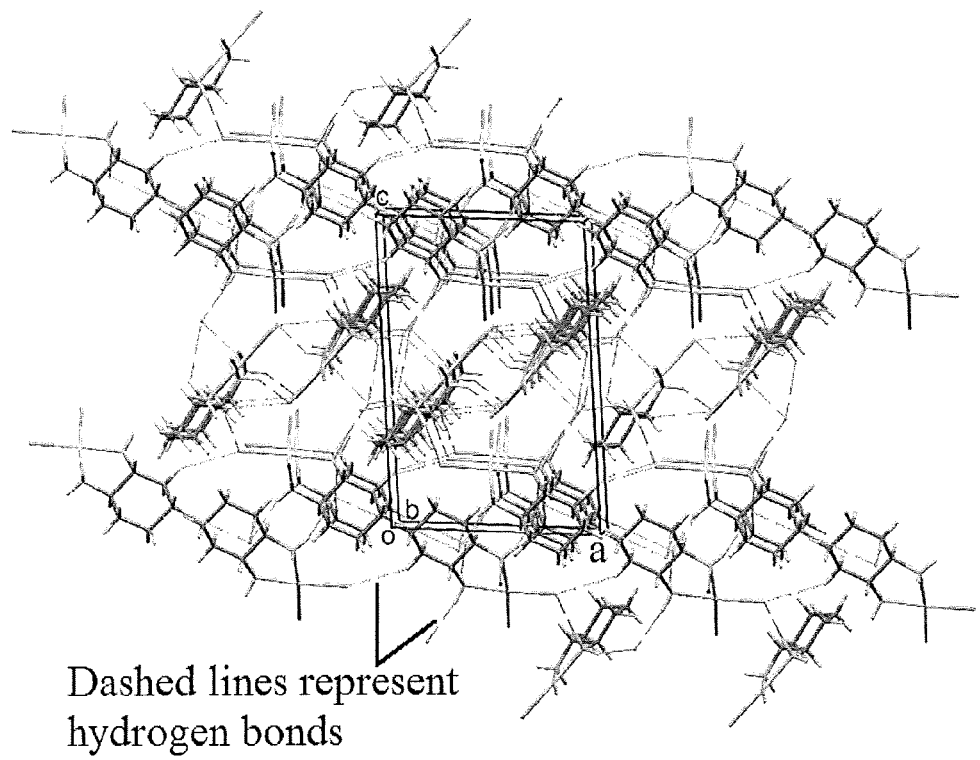
FIG. 4 shows a crystal packing of complex 1 viewed along the a-axis.

The crystal structure of complex 1 is shown in FIG. 3. The compound crystallized with two [(C$_6$H$_{14}$N$_2$)AuCl$_2$]$^+$ cations and two Cl$^-$ anions in an asymmetric unit, together with a water molecule for which it was not possible to locate the H atoms. The gold(III) ion was bonded to the two nitrogen atoms of the (1R,2R)-(−)-1,2-diaminocyclohexane ligand and two chloride ions in a distorted square planar geometry. The Au—N bond distances in molecule 1 and molecule 2 of complex 1 were in the range of 2.020(15) to 2.059(16) Å, respectively, while the Au—Cl bond distances were in the range of 2.261(5) to 2.281(5) Å, respectively, as shown in Table 7. The Cl—Au—Cl and N—Au—N bond angles were 91.4(2) to 93.71(17) and 83.2(6) to 83.7(6) ° for molecules 1 and 2, respectively. The Au—N bond distances in molecule 1 were significantly different from each other, whereas the Au—N bond distances in molecule 2 were very close to each other but different from those of molecule 1. The N—Au—N bond angle values reflected the chelation strain of the diamine ligand. These values were similar to those found in gold(III) complexes and dichloro-(trans-(±)-1,2-diaminocyclohexane)-gold(III) chloride hydrates (M. Monim-ul-Mehboob, M. Altaf, M. Fettouhi, A. A. Isab, M. I. M. Wazeer, M. N. Shaikh and S. Altuwaijri, Polyhedron, vol. 61, pp. 225-234, 2013; and S. S. Al-Jaroudi, M. Fettouhi, M. I. M. Wazeer, A. A. Isab and S. Altuwaijri, Polyhedron, vol. 50, pp. 434-442, 2013, each incorporated herein by reference in their entirety). The cyclohexyl ring adopted a chair conformation. There was a square planar geometry around the Au(III) ion, resulting in a five-membered ring formation. All the amine groups were engaged in hydrogen bonding with water molecules and the Cl$^-$ counter ions. A water molecule was present in the crystal lattice. The metal complex molecules packed head to head to generate molecular chains along the c-axis, which in turn packed into layers parallel to the ac-plane (FIG. 4).

Figure 5:
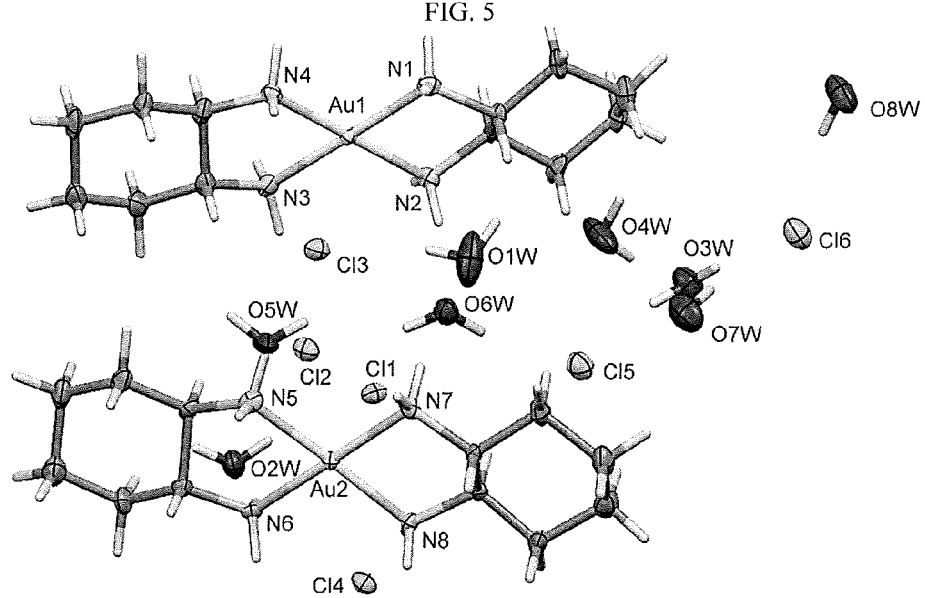
FIG. 5 is a view of the molecular structure of complex 2 with labelled atoms, and the displacement ellipsoids are drawn at the 50% probability level.
Figure 6:
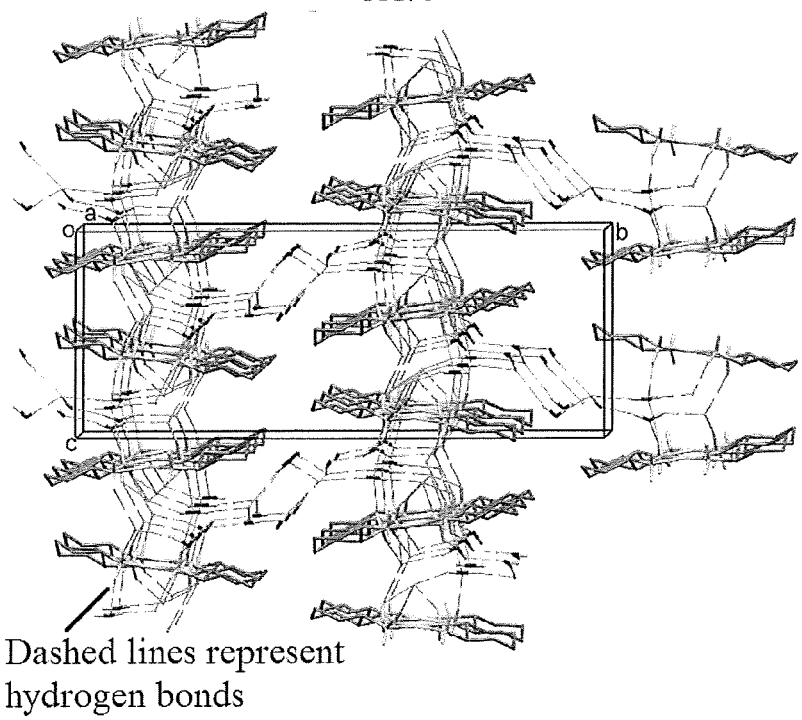
FIG. 6 shows a crystal packing of complex 2 viewed along the a-axis with hydrogen bonds represented by dashed lines, and C-bound H atoms have been omitted for clarity.
Figure 7:
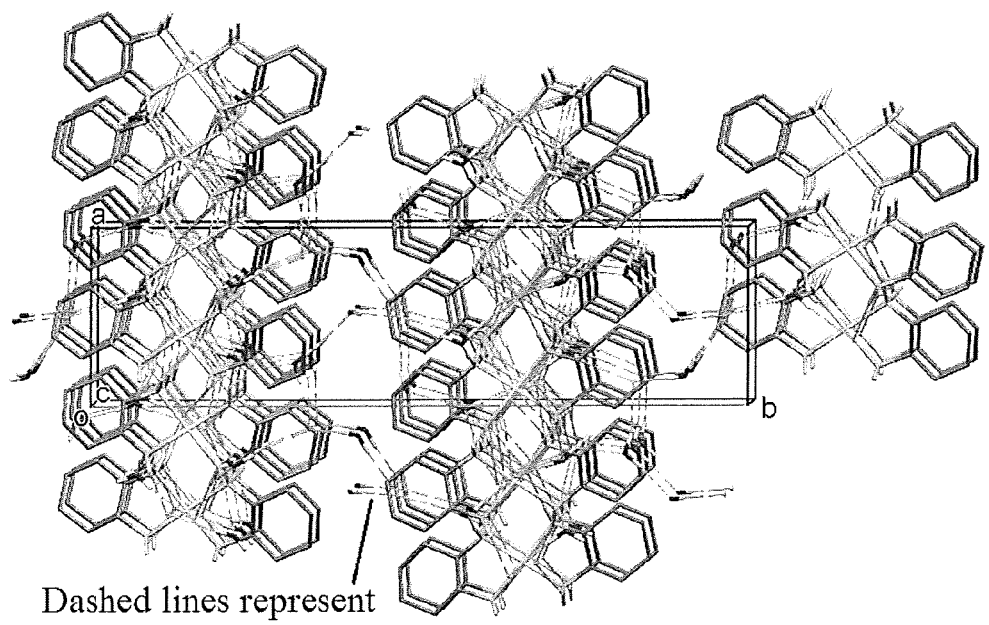
FIG. 7 shows a crystal packing of complex 2 viewed along the c-axis with hydrogen bonds represented by dashed lines, and C-bound H atoms have been omitted for clarity.
Figure 8K:
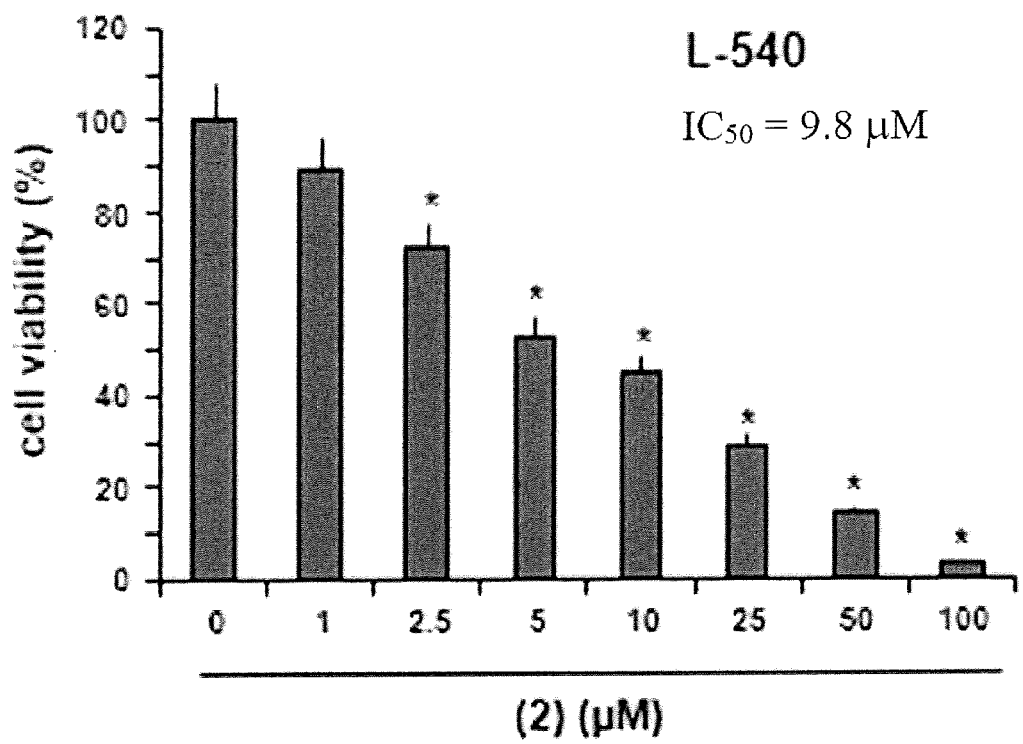
FIG. 8K is a histogram showing the percentage of living L-540 cells evaluated by a trypan blue dye exclusion assay after a 72-hour treatment with complex 2.

The X-ray structure of complex 2 is shown in FIG. 5. The compound crystallized with two [(C$_6$H$_{14}$N$_2$)$_2$Au]$^{3+}$ cations, six Cl$^-$ anions, and eight water molecules in an asymmetric unit. It was not possible to locate both H atoms on water molecules O7W and O8W. In both molecules of complex 2, the metal ion bonded to the four nitrogen atoms of two (1R,2R)-(+)-1,2-diaminocyclohexane ligands in a distorted square planar geometry. The Au—N bond distances were in the range 2.021(8)-2.048(6) Å, and the N—Au—N chelate bond angles were in the range of 83.1(2)-83.6(2) ° for molecules 1 and 2, as given in Table 7. These values were similar to those reported for [Au{trans-(±)-(1,2-DACH)}$_2$]Cl$_3$ and bis(ethylene-1,2-diamine)-gold(III) tris(perrhenate) (E. V. Makotchenko and I. A. Baidina, J. Struct. Chem., vol. 52, pp. 572-576, 2011, incorporated herein by reference in its entirety). The cyclohexyl rings adopted a chair conformation. The square planar geometry and the five-membered ring strain imposed torsion angles for N1-C1-C2-N2 of 54.0(8) ° and for N3-C7-C8-N4 of 58.3(8) ° for molecule 1, and for N5-C13-C14-N6 of 52.4(8) ° and for N7-C19-C20-N8 of 50.6(8) ° for molecule 2. The amine group hydrogen atoms were involved in hydrogen bonding interactions with Cl$^-$ counter ions and water molecules, generating a three-dimensional hydrogen bonding network, as shown in FIGS. 6 and 7.

TABLE 7

Selected bond lengths (Å) and bond angles (°) for complexes 1 and 2

| Bond Lengths (Å) | | Bond Angles (°) | |
|---|---|---|---|
| Complex 1 | | | |
| Molecule 1 | | | |
| Au1—Cl1 | 2.269(6) | Cl1—Au1—Cl2 | 91.4(2) |
| Au1—Cl2 | 2.261(5) | Cl1—Au1—N1 | 176.4(5) |
| Au1—N1 | 2.020(15) | Cl1—Au1—N2 | 92.8(5) |
| Au1—N2 | 2.059(16) | Cl2—Au1—N1 | 92.2(5) |
| | | Cl2—Au1—N2 | 175.6(5) |
| | | N1—Au1—N2 | 83.7(6) |
| Molecule 2 | | | |
| Au2—Cl3 | 2.281(5) | Cl3—Au2—Cl4 | 93.71(17) |
| Au2—Cl4 | 2.275(5) | Cl3—Au2—N3 | 173.6(5) |
| Au2—N3 | 2.041(16) | Cl3—Au2—N4 | 92.6(5) |
| Au2—N4 | 2.028(15) | Cl4—Au2—N3 | 90.5(5) |
| | | Cl4—Au2—N4 | 175.8(4) |
| | | N3—Au2—N4 | 83.2(6) |
| Complex 2 | | | |
| Molecule 1 | | | |
| Au1—N1 | 2.039(6) | N1—Au1—N2 | 83.1(2) |
| Au1—N2 | 2.044(6) | N1—Au1—N3 | 179.2(2) |
| Au1—N3 | 2.041(6) | N1—Au1—N4 | 95.6(2) |
| Au1—N4 | 2.044(6) | N2—Au1—N3 | 97.7(2) |
| | | N2—Au1—N4 | 178.2(3) |
| | | N3—Au1—N4 | 83.6(2) |
| Molecule 2 | | | |
| Au2—N7 | 2.048(6) | N7—Au2—N8 | 83.2(2) |
| Au2—N8 | 2.037(6) | N5—Au2—N8 | 177.4(3) |
| Au2—N5 | 2.021(8) | N5—Au2—N6 | 82.8(2) |
| Au2—N6 | 2.046(6) | N5—Au2—N7 | 97.6(2) |
| | | N6—Au2—N7 | 178.0(3) |
| | | N6—Au2—N8 | 96.5(2) |

EXAMPLE 7

Interaction of Gold(III) Complexes with Glutathione (GSH) and UV-vis and Kinetics Measurements All kinetics measurements were made using a UV-vis spectrophotometer (Agilent Technologies, Cary 100 UV-Vis). Scanning kinetic mode was used to investigate the change in the electronic spectra for gold(III) complexes upon interaction with GSH to determine the effective wavelength for the reactions. Then, the kinetic mode was used to monitor the reaction progress at the selected wavelength. A solution containing 0.2 mM gold(III) complexes was prepared in water, and 40 mM sodium chloride was added to improve the stability of the mononuclear-gold(III) complexes by preventing hydrolysis of the chlorides (A. Djeković, B. Petrović, Z. D. Bugarčić, R. Puchta, and R. van Eldik, *Dalton Trans.*, vol. 41, no. 13, pp. 3633-41, 2012, incorporated herein by reference in its entirety). A series of GSH solutions was also prepared. Equal volumes of gold (III) complex solution and GSH solution were mixed, and the spectral changes recorded using the scanning kinetic mode in the range from 200 nm to 350 nm. Then, the kinetic mode was used to follow the reaction at three different temperatures. The reaction between the gold(III)-diamine complexes and the GSH ligand to form gold(III)-complexes can be illustrated in following equation:

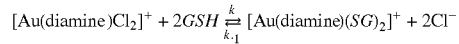

The rate (k) of the described reactions can be calculated from the slope of the linear plot of $k_{obs}$ versus GSH concentration according to eqn (1), where the rate of the reverse reaction $(k_{-1})$ is obtained from the intercept of the straight line.

$$k_{obs} = k[GSH] + k_{-1}[Cl] \qquad \text{Eqn (1)}$$

Using Microsoft Excel, the rate constants and activation parameters were calculated from Eyring plots:

$$\ln\frac{k}{T} = \frac{-\Delta H^{\ddagger}}{RT}\frac{1}{} + \ln\left(\frac{kB}{h}\right) + \frac{\Delta S^{\ddagger}}{R} \qquad \text{Eqn (2)}$$

Figure 2A:
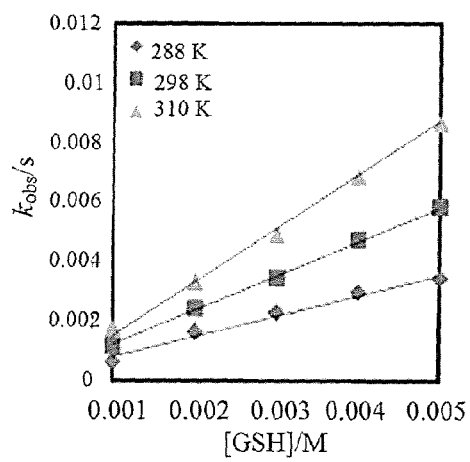
FIG. 2A is a plot of the observed rate constant against GSH concentration at various temperatures for the reaction of [(DACH)AuCl$_2$]Cl with GSH in the presence of 20 mM NaCl.
Figure 2B:
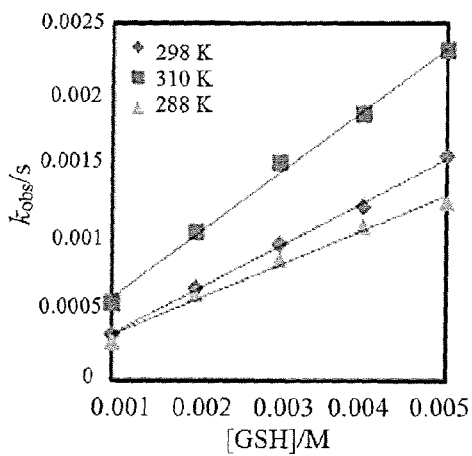
FIG. 2B is a plot of the observed rate constant against GSH concentration at various temperatures for the reaction of [(DACH)$_2$Au]Cl$_3$ with GSH in the presence of 20 mM NaCl.

The kinetics of the substitution reaction between the synthesized anticancer gold(III) complexes 1 and 2 with tripeptide glutathione were investigated spectrophotometrically by monitoring the spectral changes of the gold(III) complexes in solution with excess of GSH. A blueshift was observed in all tested compounds, and the appearance of an absorption band at 297 nm indicated the formation of a substitution product with the formula $[Au(DACH)(SG)_2]^+$. Equal volumes of the gold(III) complexes and GSH were kept until thermal equilibration was achieved and then mixed directly inside a UV cell. The changes in the absorption at a selected wavelength (297 nm) under pseudo-first order conditions as functions of the glutathione concentration and temperature were collected. The pseudo-first order rate constant (k) was obtained from the linear plot of $k_{obs}$ versus the total GSH concentration (1). NaCl was added in excess to avoid the hydrolysis of mononuclear-gold(III) diamine chloride, but this was not found to be effective for complex 2 (FIG. 2).

From the data given in Table 5, the values of the rate constants and activation parameters ($\Delta H^{\ddagger}$, $\Delta S^{\ddagger}$ and Ea) indicate that complex 1 reacts three times faster than complex 2 in a substitution reaction with GSH due to several factors related to the environment around the gold(III) center. This difference in reactivity can be attributed to ease of the chloride replacement by the GSH sulfur atom in complex 1 to form the short lifetime intermediate $[Au(DACH)(SG)_2]^+$ at 297 nm. However, the DACH ligand geometry also played a very important role in the reactivity of the gold(III) center, as the chair conformation of DACH in its gold(III) complexes increased the stability by hindering GSH attack. Thus, the rate constant increased by a factor of 3. The decrease in the electrophilicity of the metal center due to the electronic inductive effects of cyclohexyl in complex 2 also contributed to a slower reaction rate. The negative entropy of activation may be rationalized in terms of the formation of the intermediate, where two bulky GSH molecules are tied to the complexes, thereby reducing the entropy through the decrease in the number of reacting species.

TABLE 5

Kinetic data for the reaction of synthesized gold(III) complexes with GSH

| Complex | $^a$k (M$^{-1}$·s$^{-1}$) | ΔH$^≠$ (kJ·mol$^{-1}$) | ΔS$^≠$ (JK$^{-1}$mol$^{-1}$) | Ea (kJ·mol$^{-1}$) |
|---|---|---|---|---|
| (1) | 114 × 10$^{-2}$ | 30 | −137 | 32 |
| (2) | 31 × 10$^{-2}$ | 17 | −189 | 19 |

$^a$Pseudo-first order rate constant at 298 K.

EXAMPLE 8

In vitro Cytotoxic Assay for Synthesized Gold(III) Complexes

Complexes 1 and 2 were dissolved (10 mM) in DMSO and stored at −80° C. at volumes of 500 μL or aliquots with volumes of 10 μL were taken and stored at −20° C. (used once without refreezing). The compounds were then diluted in RPMI medium immediately before use. Cisplatin was purchased from Mayne Pharma. Culture medium with the same amount of drug-free DMSO was used as a negative control.

The classical Hodgkin lymphoma L-540 cell line was obtained from the German Collection of Microorganisms and Cell Cultures (Braunschweig, Germany). Human ovarian epithelial carcinoma-derived cancer cells A2780 and its cisplatin-resistant clone A2780cis were from Sigma, Inc. (St. Louis, Mo., USA). The parent cisplatin-resistant subclone A2780cis was maintained by weekly treatment with 1 μM cisplatin (N. Casagrande, M. Celegato, C. Borghese, M. Mongiat, A. Colombatti, and D. Aldinucci, Clin. Cancer Res. vol. 20, pp. 5496-5506, 2014, incorporated herein by reference in its entirety). Cells were cultured at 37° C. in 5% CO$_2$ in RPMI medium supplemented with 10% heat-inactivated FBS, 0.1% (w/v) L-glutamine and antibiotics (0.2 mg/mL penicillin and streptomycin).

For the cell proliferation assay, 4.0×10$^3$ A2780 and A2780cis cells were seeded in 96-well flat-bottomed microplates in RPMI medium (100 μL) and incubated at 37° C. in a 5% CO$_2$ atmosphere for 24 h (to allow cell adhesion) before drug testing. The medium was then removed and replaced with fresh medium containing the compounds to be tested and cisplatin at increasing concentrations (from 1 to 100 μM) at 37° C. for 72 h. Each treatment was performed in triplicate. Cell proliferation was assayed using the MTT assay. L-540 cells (2.0×10$^5$/ml) were seeded in 48-well plates and treated with increasing concentrations of complex 1 and complex 2. After 72 hours, the number of viable cells was evaluated by a trypan blue dye exclusion.

The IC$_{50}$ values (i.e., the half maximal inhibitory concentration, representing the concentration of a substance required for 50% inhibition in vitro) were calculated using CalcuSyn software (Biosoft, Ferguson, Mo., USA) (T. C. Chou, and P. Talalay, Adv. Enzyme Regul. vol. 22, pp. 27-55, 1984, incorporated herein by reference in its entirety). The results were presented as the mean±SEM of three replicate wells from three independent experiments. The cells were imaged under an inverted microscope (Eclipse TS/100, Nikon) with a photomicrographic system (DS Camera Control Unit DS-L2). Phase contrast micrographs were taken at a magnification of 4× (for L-540 cells) and 10× (for A2780 and A2780cis cells).

Statistical analysis was performed on the data using GraphPad Software. The significance of the differences was determined by Student's t-test for comparison between two groups. P<0.05 was considered statistically significant. The symbol "*" in FIGS. 8J, 8K, 9S, and 9T denotes P<0.05 for gold complex versus control medium.

The in vitro antiproliferative activity of complexes 1 and 2 in the classical Hodgkin lymphoma-derived cell line L-540 was evaluated (FIGS. 8A-8K). Exposure of L-540 cells to increasing concentrations of both gold complexes resulted in a dose-dependent cytotoxic activity, as shown in representative micrographs (FIGS. 8B-8I). Complex 2 exhibited a more potent inhibition of cell growth compared to complex 1 (FIGS. 8J and 8K), as evaluated by the trypan blue assay. Complex 2 was 7-fold more active than complex 1, with IC$_{50}$ values of 9.8 μM and 70.4 μM, respectively.

Figure 9S:
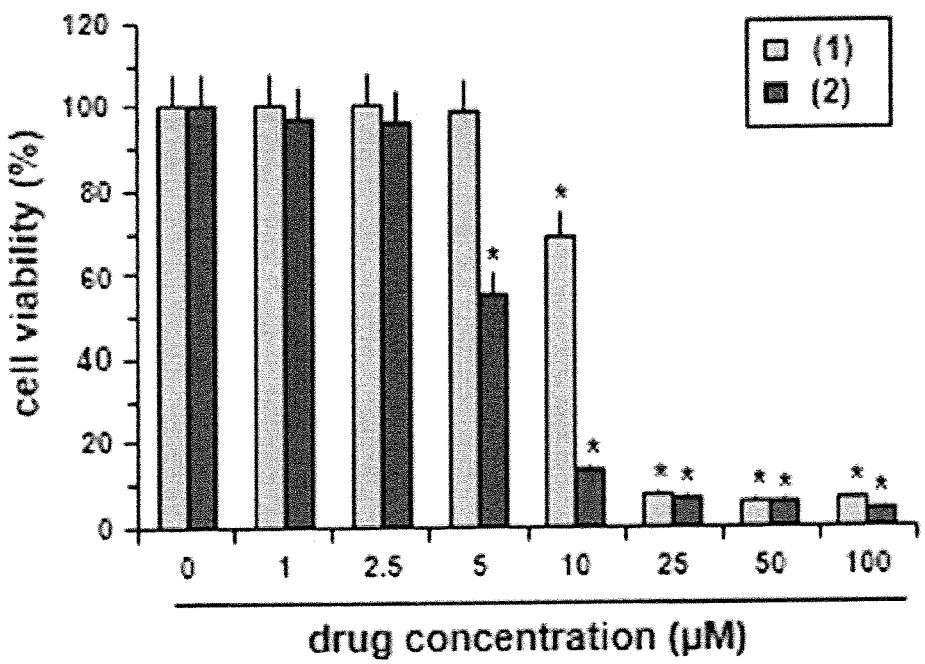
FIG. 9S is a histogram showing the percentage of living A2780 cells evaluated by a MTT assay after a 72-hour treatment with complex 1 and complex 2.
Figure 9T:
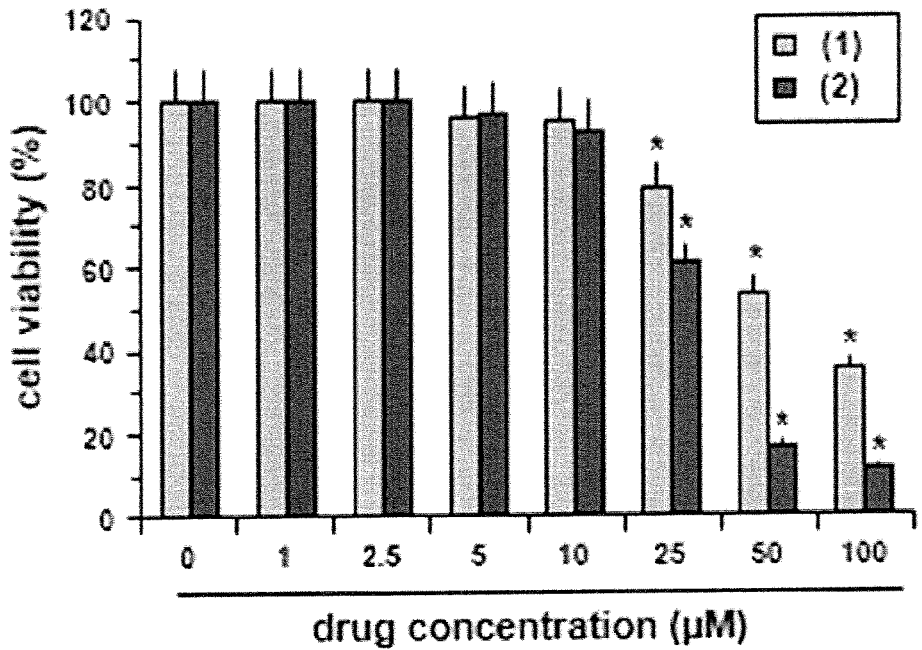
FIG. 9T is a histogram showing the percentage of living A2780cis cells evaluated by a MTT assay after a 72-hour treatment with complex 1 and complex 2.

The cytotoxic activities of gold complexes 1 and 2 were also evaluated in the ovarian carcinoma-derived cell line A2780 and in its cisplatin-resistant clone (A2780cis) using the MTT assay. For comparison purposes, the cisplatin activity was evaluated under the same experimental conditions. Both compounds inhibited proliferation in a dose-dependent manner (FIGS. 9B-9I and 9K-9R). Again, complex 2 exhibited a more potent inhibition of cell growth compared with complex 1 in both A2780 (FIG. 9S) and A2780cis cells (FIG. 9T).

The IC$_{50}$ values of complex 1 were 61.3 μM for A2780cis and 15.7 μM for A2780 cells, and for complex 2, the IC$_{50}$ values were 31.1 μM for A2780cis and 6.98 μM for A2780 (Table 8). The IC$_{50}$ values for cisplatin in A2780cis and A2780 were 17.6 and 1.8 μM, respectively, showing a 9.7-increase in resistance (fold resistance) to cisplatin in A2780cis compared with A2780 (Table 8). Although the IC$_{50}$ values for both gold complexes were higher than those for cisplatin in A2780 and A2780cis cells, the fold-resistances of both complexes were approximately two-fold lower than that of cisplatin (Table 8).

TABLE 8

Growth inhibition by complexes 1 and 2 in A2780 and A2780cis ovarian cancer cells

| Complex | IC$_{50}$ (μM) | | Fold resistance A2780cis/A2780 |
|---|---|---|---|
| | A2780 | A2780cis | ratio |
| Cisplatin | 1.8 ± 0.1 | 17.6 ± 1.5 | 9.77 |
| (1) | 15.7 ± 1.4 | 61.3 ± 5.5 | 3.90 |
| (2) | 6.9 ± 0.6 | 31.1 ± 2.8 | 4.45 |

Altogether, these results indicate the higher cytotoxic potential of compound 2 with respect to compound 1 and the decreased fold-resistance of both compounds with respect to cisplatin.

The foregoing discussion discloses and describes merely exemplary embodiments of the present disclosure. As will be understood by those skilled in the art, the present disclosure may be embodied in other specific forms without departing from the spirit or essential characteristics thereof. Accordingly, the disclosure of the present disclosure is intended to be illustrative, but not limiting of the scope of the disclosure, as well as other claims. The disclosure, including any readily discernible variants of the teachings herein, defines, in part, the scope of the foregoing claim terminology such that no inventive subject matter is dedicated to the public.

The invention claimed is:
1. A pharmaceutical composition, comprising:
at least one oil solvent selected from the group consisting of cocoa butter, a mono-glyceride, a di-glyceride, a tri-glyceride, a fatty acid and a polyethylene glycol, and
at least one of a gold(III) complex represented by formula (I) and a gold(III) complex represented by formula (II):

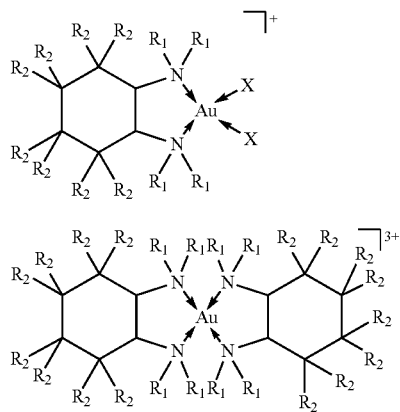

or a pharmaceutically acceptable salt, solvate, or prodrug thereof;
wherein each $R_1$ is independently selected from the group consisting of isopropyl, butyl, isobutyl, t-butyl, pentyl, isopentyl, neopentyl, hexyl, isohexyl, 3-methylpentyl, 2,2-dimethylbutyl, and 2,3-dimethylbutyl;
each of $R_2$ is independently selected from the group consisting of a hydrogen, a halogen, a hydroxyl, an amino, a nitro, a cyano, an optionally substituted alkyl, an optionally substituted cycloalkyl, an optionally substituted heterocyclyl, an optionally substituted arylalkyl, an optionally substituted heteroaryl, an optionally substituted alkoxyl, an optionally substituted aryl, an optionally substituted alkenyl, a N-monosubstituted amino group, and a N,N-disubstituted amino group;
X is selected from the group consisting of chloride, bromide, and iodide; and
the gold (III) complex comprises at least one pharmaceutically acceptable anion selected from the group consisting of salicylate, malate, maleate, succinate, tartrate, citrate and acetate.

2. The pharmaceutical composition of claim 1, comprising the gold(III) complex of formula (I), wherein X is chloride.

3. The pharmaceutical composition of claim 1, comprising the gold(III) complex of formula (II) wherein the at least one pharmaceutically acceptable anion is acetate.

4. The pharmaceutical composition of claim 1, wherein each $R_1$ is independently selected from the group consisting of butyl, isobutyl, t-butyl, pentyl, isopentyl, neopentyl, hexyl, isohexyl, 3-methylpentyl, 2,2-dimethylbutyl, and 2,3-dimethylbutyl.

5. The pharmaceutical composition of claim 1, wherein $R_1$ is isopropyl, $R_2$ is hydrogen, X is chloride, the oil solvent comprises a polyethylene glycol and the pharmaceutically acceptable anion is acetate.

6. The pharmaceutical composition of claim 1, wherein $R_1$ is butyl, $R_2$ is hydrogen, X is chloride, the oil solvent comprises a polyethylene glycol and the pharmaceutically acceptable anion is acetate.

* * * * *